United States Patent
Cadwell

(10) Patent No.: US 11,185,684 B2
(45) Date of Patent: Nov. 30, 2021

(54) MINIMALLY INVASIVE TWO-DIMENSIONAL GRID ELECTRODE

(71) Applicant: Cadwell Laboratories, Inc., Kennewick, WA (US)

(72) Inventor: John A. Cadwell, Richland, WA (US)

(*) Notice: Subject to any disclaimer, the term of this patent is extended or adjusted under 35 U.S.C. 154(b) by 148 days.

(21) Appl. No.: 16/574,824

(22) Filed: Sep. 18, 2019

(65) Prior Publication Data
US 2020/0108246 A1  Apr. 9, 2020

Related U.S. Application Data

(60) Provisional application No. 62/767,504, filed on Nov. 14, 2018, provisional application No. 62/732,654, filed on Sep. 18, 2018.

(51) Int. Cl.
*A61N 1/05* (2006.01)
*A61N 1/372* (2006.01)
*A61N 1/36* (2006.01)

(52) U.S. Cl.
CPC ....... *A61N 1/0539* (2013.01); *A61N 1/37205* (2013.01); *A61N 1/36064* (2013.01)

(58) Field of Classification Search
None
See application file for complete search history.

(56) References Cited

U.S. PATENT DOCUMENTS

| | | |
|---|---|---|
| 751,475 A | 2/1904 | Vilbiss |
| 2,320,709 A | 6/1943 | Arnesen |
| 2,807,259 A | 9/1957 | Guerriero |
| 3,165,340 A | 1/1965 | Kuehl |
| 3,659,250 A | 4/1972 | Horton |
| 3,682,162 A | 8/1972 | Colyer |
| 3,985,125 A | 10/1976 | Rose |
| 3,993,859 A | 11/1976 | McNeel |
| 4,155,353 A | 5/1979 | Rea |

(Continued)

FOREIGN PATENT DOCUMENTS

| | | |
|---|---|---|
| DE | 102014008684 A1 | 1/2016 |
| EP | 298268 | 1/1989 |

(Continued)

OTHER PUBLICATIONS

Aage R. Møller, "Intraoperative Neurophysiologic Monitoring", University of Pittsburgh, School of Medicine Pennsylvania, © 1995 by Harwood Academic Publishers GmbH.

(Continued)

*Primary Examiner* — Brian T Gedeon
(74) *Attorney, Agent, or Firm* — Novel IP

(57) ABSTRACT

A system for deploying an electrode array at a target location through a hole formed in the patient's cranium. The system includes an array of electrodes attached to a substrate and an inserter attached to the substrate and/or the array of electrodes. The inserter, substrate and array of electrodes are configured into a first compressed state and are positioned within the lumen of a cannula. Using the cannula, the system is inserted through the hole, the cannula is then removed, and the inserter is used to transition the substrate and electrode array from the first compressed state to a second uncompressed state, thereby deploying the array of electrodes at the target location.

42 Claims, 15 Drawing Sheets

(56) References Cited

U.S. PATENT DOCUMENTS

| | | |
|---|---|---|
| 4,262,306 A | 4/1981 | Karlheinz |
| 4,263,899 A | 4/1981 | Burgin |
| 4,545,374 A | 10/1985 | Jacobson |
| 4,562,832 A | 1/1986 | Wilder |
| 4,616,635 A | 10/1986 | Caspar |
| 4,705,049 A | 11/1987 | John |
| 4,716,901 A | 1/1988 | Jackson |
| 4,743,959 A | 5/1988 | Frederiksen |
| 4,765,311 A | 8/1988 | Kulik |
| 4,817,587 A | 4/1989 | Janese |
| 4,862,891 A | 9/1989 | Smith |
| 4,889,502 A | 12/1989 | Althouse |
| 4,914,508 A | 4/1990 | John |
| 5,107,845 A | 4/1992 | Yves |
| 5,171,279 A | 12/1992 | Mathews |
| 5,196,015 A | 3/1993 | Neubardt |
| 5,284,153 A | 2/1994 | Raymond |
| 5,284,154 A | 2/1994 | Raymond |
| 5,299,563 A | 4/1994 | Seton |
| 5,377,667 A | 1/1995 | Patton |
| 5,438,989 A | 8/1995 | Darryl |
| 5,462,448 A | 10/1995 | Kida |
| 5,472,426 A | 12/1995 | Bonati |
| 5,474,558 A | 12/1995 | Neubardt |
| 5,540,235 A | 7/1996 | Wilson |
| 5,544,286 A | 8/1996 | Laney |
| 5,560,372 A | 10/1996 | Cory |
| 5,565,779 A | 10/1996 | Arakawa |
| 5,578,060 A | 11/1996 | Pohl |
| 5,601,608 A | 2/1997 | Mouchawar |
| 5,602,585 A | 2/1997 | Dickinson |
| 5,625,759 A | 4/1997 | Freeman |
| 5,648,815 A | 7/1997 | Akira |
| 5,664,029 A | 9/1997 | Callahan |
| 5,681,265 A | 10/1997 | Maeda |
| 5,684,887 A | 11/1997 | Lee |
| 5,728,046 A | 3/1998 | Mayer |
| 5,741,261 A | 4/1998 | Moskovitz |
| 5,772,661 A | 6/1998 | Michelson |
| 5,775,331 A | 7/1998 | Raymond |
| 5,775,931 A | 7/1998 | Boyd |
| 5,785,648 A | 7/1998 | Min |
| 5,792,044 A | 8/1998 | Foley |
| 5,795,291 A | 8/1998 | Koros |
| 5,830,150 A | 11/1998 | Palmer |
| 5,847,755 A | 12/1998 | Wixson |
| 5,860,973 A | 1/1999 | Michelson |
| 5,868,668 A | 2/1999 | Weiss |
| 5,885,210 A | 3/1999 | Cox |
| 5,891,147 A | 4/1999 | Moskovitz |
| 5,928,139 A | 7/1999 | Koros |
| 5,928,158 A | 7/1999 | Aristides |
| 5,930,379 A | 7/1999 | Rehg |
| 5,931,777 A | 8/1999 | Sava |
| 5,933,929 A | 8/1999 | Katsunori |
| 5,944,658 A | 8/1999 | Koros |
| 5,954,635 A | 9/1999 | Foley |
| 5,993,385 A | 11/1999 | Johnston |
| 6,004,312 A | 12/1999 | Finneran |
| 6,004,341 A | 12/1999 | Zhu |
| 6,026,180 A | 2/2000 | Andreas |
| 6,042,540 A | 3/2000 | Johnston |
| 6,062,216 A | 5/2000 | Corn |
| 6,074,343 A | 6/2000 | Nathanson |
| 6,088,878 A | 7/2000 | Antonucci |
| 6,095,987 A | 8/2000 | Shmulewitz |
| 6,109,948 A | 8/2000 | Peter |
| 6,116,941 A | 9/2000 | Peter |
| 6,119,306 A | 9/2000 | Antonucci |
| 6,139,493 A | 10/2000 | Koros |
| 6,152,871 A | 11/2000 | Foley |
| 6,181,961 B1 | 1/2001 | Prass |
| 6,196,969 B1 | 3/2001 | Bester |
| 6,206,826 B1 | 3/2001 | Mathews |
| 6,210,202 B1 | 4/2001 | Peter |
| 6,224,545 B1 | 5/2001 | Cocchia |
| 6,236,874 B1 | 5/2001 | Devlin |
| 6,241,548 B1 | 6/2001 | Peter |
| 6,259,945 B1 | 7/2001 | Epstein |
| 6,264,491 B1 | 7/2001 | Charles |
| 6,266,558 B1 | 7/2001 | Gozani |
| 6,273,740 B1 | 8/2001 | Charles |
| 6,287,322 B1 | 9/2001 | Zhu |
| 6,302,842 B1 | 10/2001 | Auerbach |
| 6,306,100 B1 | 10/2001 | Prass |
| 6,309,349 B1 | 10/2001 | Bertolero |
| 6,325,764 B1 | 12/2001 | Griffith |
| 6,334,068 B1 | 12/2001 | Hacker |
| 6,373,890 B1 | 4/2002 | Freeman |
| 6,425,859 B1 | 7/2002 | Foley |
| 6,450,952 B1 | 9/2002 | Rioux |
| 6,466,817 B1 | 10/2002 | Kaula |
| 6,473,639 B1 | 10/2002 | Fischell |
| 6,500,128 B2 | 12/2002 | Marino |
| 6,535,759 B1 | 3/2003 | Epstein |
| 6,579,114 B2 | 6/2003 | Charles |
| 6,609,018 B2 | 8/2003 | Cory |
| 6,712,795 B1 | 3/2004 | Cohen |
| 6,799,931 B2 | 10/2004 | Kwilosz |
| 6,805,668 B1 | 10/2004 | Cadwell |
| 6,837,716 B1 | 1/2005 | Brazas |
| 6,847,849 B2 | 1/2005 | Mamo |
| 6,851,430 B2 | 2/2005 | Tsou |
| 6,869,301 B2 | 3/2005 | Shinji |
| 6,870,109 B1 | 3/2005 | Villarreal |
| 6,926,728 B2 | 8/2005 | Zucherman |
| 6,945,933 B2 | 9/2005 | Branch |
| 7,072,521 B1 | 7/2006 | Cadwell |
| 7,089,059 B1 | 8/2006 | Pless |
| 7,104,965 B1 | 9/2006 | Jiang |
| 7,177,677 B2 | 2/2007 | Kaula |
| 7,214,197 B2 | 5/2007 | Prass |
| 7,230,688 B1 | 6/2007 | Villarreal |
| 7,261,688 B2 | 8/2007 | Smith |
| 7,374,448 B1 | 5/2008 | Jepsen |
| 7,470,236 B1 | 12/2008 | Kelleher |
| 7,522,953 B2 | 4/2009 | Kaula |
| 7,713,210 B2 | 5/2010 | Byrd |
| 7,801,601 B2 | 9/2010 | Maschino |
| 7,914,350 B1 | 3/2011 | Bozich |
| 7,963,927 B2 | 6/2011 | Kelleher |
| 7,983,761 B2 | 7/2011 | Giuntoli |
| 8,147,421 B2 | 4/2012 | Farquhar |
| 8,160,694 B2 | 4/2012 | Salmon |
| 8,192,437 B2 | 6/2012 | Simonson |
| D670,656 S | 11/2012 | Lee |
| 8,323,208 B2 | 12/2012 | Taylor |
| 8,439,703 B2 | 5/2013 | Natoli |
| 8,876,813 B2 | 11/2014 | Min |
| 8,942,797 B2 | 1/2015 | Bartol |
| 8,958,869 B2 | 2/2015 | Kelleher |
| 9,084,551 B2 | 7/2015 | Brunnett |
| 9,138,586 B2 | 9/2015 | Eiger |
| 9,155,503 B2 | 10/2015 | Cadwell |
| 9,295,401 B2 | 3/2016 | Cadwell |
| 9,352,153 B2 | 5/2016 | Van Dijk |
| 9,730,634 B2 | 8/2017 | Cadwell |
| 10,238,467 B2 | 3/2019 | Cadwell |
| 2002/0007188 A1 | 1/2002 | Arambula |
| 2002/0009916 A1 | 1/2002 | Charles |
| 2002/0088098 A1 | 7/2002 | Bouley |
| 2002/0095080 A1 | 7/2002 | Cory |
| 2003/0045808 A1 | 3/2003 | Kaula |
| 2003/0074033 A1 | 4/2003 | Pless |
| 2004/0030258 A1 | 2/2004 | Williams |
| 2004/0127810 A1 | 7/2004 | Sackellares |
| 2004/0192100 A1 | 9/2004 | Shimizu |
| 2005/0003682 A1 | 1/2005 | Brazas |
| 2005/0075578 A1 | 4/2005 | Gharib |
| 2005/0182454 A1 | 8/2005 | Gharib |
| 2006/0009754 A1 | 1/2006 | Boese |
| 2006/0085048 A1 | 4/2006 | Cory |
| 2006/0085049 A1 | 4/2006 | Cory |
| 2006/0122514 A1 | 6/2006 | Byrd |

(56) References Cited

U.S. PATENT DOCUMENTS

| | | |
|---|---|---|
| 2006/0135877 A1 | 6/2006 | Giftakis |
| 2006/0258951 A1 | 11/2006 | Bleich |
| 2007/0016097 A1 | 1/2007 | Farquhar |
| 2007/0021682 A1 | 1/2007 | Gharib |
| 2007/0032841 A1 | 2/2007 | Urmey |
| 2007/0049962 A1 | 3/2007 | Marino |
| 2007/0184422 A1 | 8/2007 | Takahashi |
| 2007/0202005 A1 | 8/2007 | Michael |
| 2008/0027507 A1 | 1/2008 | Bijelic |
| 2008/0058606 A1 | 3/2008 | Miles |
| 2008/0065144 A1 | 3/2008 | Marino |
| 2008/0071191 A1 | 3/2008 | Kelleher |
| 2008/0082136 A1 | 4/2008 | Gaudiani |
| 2008/0097164 A1 | 4/2008 | Miles |
| 2008/0108244 A1 | 5/2008 | Jepsen |
| 2008/0167574 A1 | 7/2008 | Farquhar |
| 2008/0183096 A1 | 7/2008 | Snyder |
| 2008/0194970 A1 | 8/2008 | Steers |
| 2008/0269777 A1 | 10/2008 | Appenrodt |
| 2008/0281313 A1 | 11/2008 | Fagin |
| 2008/0312520 A1 | 12/2008 | Rowlandson |
| 2009/0018399 A1 | 1/2009 | Martinelli |
| 2009/0088660 A1 | 4/2009 | McMorrow |
| 2009/0105604 A1 | 4/2009 | Bertagnoli |
| 2009/0177112 A1 | 7/2009 | Gharib |
| 2009/0196471 A1 | 8/2009 | Goetz |
| 2009/0204016 A1 | 8/2009 | Gharib |
| 2009/0209879 A1 | 8/2009 | Kaula |
| 2009/0259108 A1 | 10/2009 | Miles |
| 2009/0279767 A1 | 11/2009 | Kukuk |
| 2010/0036384 A1 | 2/2010 | Gorek |
| 2010/0106011 A1 | 4/2010 | Byrd |
| 2010/0113898 A1 | 5/2010 | Youn-Ho |
| 2010/0152604 A1 | 6/2010 | Kaula |
| 2010/0168603 A1 | 7/2010 | Himes |
| 2010/0191305 A1 | 7/2010 | Imran |
| 2010/0249638 A1 | 9/2010 | Liley |
| 2010/0286554 A1 | 11/2010 | Davis |
| 2010/0317931 A1 | 12/2010 | Sarkela |
| 2010/0317989 A1 | 12/2010 | Gharib |
| 2011/0082383 A1 | 4/2011 | Cory |
| 2011/0184308 A1 | 7/2011 | Kaula |
| 2011/0295579 A1 | 12/2011 | Tang |
| 2011/0313530 A1 | 12/2011 | Gharib |
| 2012/0003862 A1 | 1/2012 | Richard |
| 2012/0071779 A1 | 3/2012 | Sarkela |
| 2012/0109000 A1 | 5/2012 | Kaula |
| 2012/0109004 A1 | 5/2012 | John |
| 2012/0209082 A1 | 8/2012 | Al-Ali |
| 2012/0220891 A1 | 8/2012 | Kaula |
| 2012/0238893 A1 | 9/2012 | Farquhar |
| 2012/0265040 A1 | 10/2012 | Ito |
| 2012/0296230 A1 | 11/2012 | Davis |
| 2013/0012880 A1 | 1/2013 | Blomquist |
| 2013/0109996 A1 | 5/2013 | Turnbull |
| 2013/0138010 A1 | 5/2013 | Nicolas |
| 2013/0152657 A1* | 6/2013 | Swinehart ............ B21D 21/00 72/369 |
| 2013/0304407 A1 | 11/2013 | George |
| 2014/0121555 A1 | 5/2014 | Scott |
| 2014/0275926 A1 | 9/2014 | Scott |
| 2014/0276181 A1 | 9/2014 | Felice |
| 2015/0230749 A1 | 8/2015 | Gharib |
| 2015/0372433 A1 | 12/2015 | Daniel |
| 2016/0000382 A1 | 1/2016 | Jain |
| 2016/0174861 A1 | 6/2016 | Cadwell |
| 2016/0328991 A1 | 11/2016 | Simpson |
| 2018/0117309 A1* | 5/2018 | Rapoport ............ A61N 1/36067 |
| 2018/0161123 A1 | 6/2018 | Cadwell |
| 2018/0198218 A1 | 7/2018 | Regan |
| 2019/0190187 A1 | 6/2019 | Takeki |
| 2020/0330772 A1 | 10/2020 | Kathy |

FOREIGN PATENT DOCUMENTS

| | | |
|---|---|---|
| EP | 0863719 A1 | 9/1998 |
| EP | 890341 | 1/1999 |
| EP | 972538 | 1/2000 |
| EP | 1182965 B1 | 3/2002 |
| EP | 2173238 A2 | 4/2010 |
| WO | 2000038574 A1 | 7/2000 |
| WO | 2000066217 A1 | 11/2000 |
| WO | 2001037728 A1 | 5/2001 |
| WO | 2003005887 A2 | 1/2003 |
| WO | 2005030318 A1 | 4/2005 |
| WO | 2006042241 A2 | 4/2006 |
| WO | 2016028822 A1 | 2/2016 |

OTHER PUBLICATIONS

Clements, et al., "Evoked and Spontaneous Electromyography to Evaluate Lumbosacral Pedicle Screw Placement", 21 (5):600-604 (1996).

Danesh-Clough, et al., "The Use of Evoked EMG in Detecting Misplaced Thoracolumbar Pedicle Screws", 26(12):1313-1316 (2001).

Dezawa et al., "Retroperitoneal Laparoscopic Lateral Approach to the Lumbar Spine: A New Approach, Technique, and Clinical Trial", Journal of Spinal Disorders 13(2):138-143 (2000).

Dickman, et al., "Techniques in Neurosurgery", National Library of Medicine, 3 (4) 301-307 (1997).

Epstein, et al., "Evaluation of Intraoperative Somatosensory-Evoked Potential Monitoring During 100 Cervical Operations", 18(6):737-747 (1993), J.B. Lippincott Company.

Glassman, et al., "A Prospective Analysis of Intraoperative Electromyographic Monitoring of Pedicle Screw Placement with Computed Tomographic Scan Confirmation", 20(12):1375-1379.

Goldstein, et al., "Minimally Invasive Endoscopic Surgery of the Lumbar Spine", Operative Techniques in Orthopaedics, 7 (1):27-35 (1997).

Greenblatt, et al., "Needle Nerve Stimulator-Locator", 41 (5):599-602 (1962).

H.M. Mayer, "Minimally Invasive Spine Surgery, A Surgical Manual", Chapter 12, pp. 117-131 (2000).

Hinrichs, et al., "A trend-detection algorithm for intraoperative EEG monitoring", Med. Eng. Phys. 18(8):626-631 (1996).

Bergey et al., "Endoscopic Lateral Transpsoas Approach to the Lumbar Spine", SPINE 29(15):1681-1688 (2004).

Holland, "Spine Update, Intraoperative Electromyography During Thoracolumbar Spinal Surgery", 23(17):1915-1922 (1998).

Holland, et al., "Continuous Electromyographic Monitoring to Detect Nerve Root Injury During Thoracolumbar Scoliosis Surgery", 22 (21):2547-2550 (1997), Lippincott-Raven Publishers.

Hovey, A Guide to Motor Nerve Monitoring, pp. 1-31 Mar. 20, 1998, The Magstim Company Limited.

Kevin T. Foley, et al., "Microendoscipic Discectomy" Techniques in Neurosurgery, 3:(4):301-307, © 1997 Lippincott-Raven Publishers, Philadelphia.

Kossmann et al., "The use of a retractor system (SynFrame) for open, minimal invasive reconstruction of the anterior column of the thoracic and lumbar spine", 10:396-402 (2001).

Kossmann, et al., "Minimally Invasive Vertebral Replacement with Cages in Thoracic and Lumbar Spine", European Journal of Trauma, 2001, No. 6, pp. 292-300.

Lenke, et al., "Triggered Electromyographic Threshold for Accuracy of Pedicle Screw Placement, An Animal Model and Clinical Correlation", 20 (14):1585-1591 (1995).

Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.

MaGuire, et al., "Evaluation of Intrapedicular Screw Position Using Intraoperative Evoked Electromyography", 20 (9):1068-1074 (1995).

Mathews et al., "Laparoscopic Discectomy With Anterior Lumbar Interbody Fusion, A Preliminary Review", 20 (16):1797-1802, (1995), Lippincott-Raven Publishers.

(56) References Cited

OTHER PUBLICATIONS

Bertagnoli, et al., "The AnteroLateral transPsoatic Approach (ALPA), A New Technique for Implanting Prosthetic Disc-Nucleus Devices", 16 (4):398-404 (2003).

Michael R. Isley, et al., "Recent Advances in Intraoperative Neuromonitoring of Spinal Cord Function: Pedicle Screw Stimulation Techniques", Am. J. End Technol. 37:93-126 (1997).

Minahan, et al., "The Effect of Neuromuscular Blockade on Pedicle Screw Stimulation Thresholds" 25(19):2526-2530 (2000).

Pimenta et al., "Implante de prótese de núcleo pulposo: análise inicial", J Bras Neurocirurg 12(2):93-96, (2001).

Raymond J. Gardocki, MD, "Tubular diskectomy minimizes collateral damage", AAOS Now, Sep. 2009 Issue, http://www.aaos.org/news/aaosnow/Sep09/clinical12.asp.

Raymond, et al., "The NerveSeeker: A System for Automated Nerve Localization", Regional Anesthesia 17:151-162 (1992).

Reidy, et al., "Evaluation of electromyographic monitoring during insertion of thoracic pedicle screws", British Editorial Society of Bone and Joint Surgery 83 (7):1009-1014, (2001).

Rose et al., "Persistently Electrified Pedicle Stimulation Instruments in Spinal Instrumentation: Technique and Protocol Development", Spine: 22(3): 334-343 (1997).

Teresa Riordan "Patents; A businessman invents a device to give laparoscopic surgeons a better view of their worK", New York Times www.nytimes.com/2004/29/business/patents-businessman-invents-device-give-la (Mar. 2004).

Toleikis, et al., "The usefulness of Electrical Stimulation for Assessing Pedicle Screw Placements", Journal of Spinal Disorders, 13 (4):283-289 (2000).

U.Schick, et al., "Microendoscopic lumbar discectomy versus open surgery: an intraoperative EMG study", pp. 20-26, Published online: Jul. 31, 2001 © Springer-Verlag 2001.

Bose, et al., "Neurophysiologic Monitoring of Spinal Nerve Root Function During Instrumented Posterior Lumbar Spine Surgery", 27 (13):1440-1450 (2002).

Vaccaro, et al., "Principles and Practice of Spine Surgery", Mosby, Inc. © 2003, Chapter 21, pp. 275-281.

Vincent C. Traynelis, "Spinal arthroplasty", Neurosurg Focus 13 (2):1-7. Article 10, (2002).

Welch, et al., "Evaluation with evoked and spontaneous electromyography during lumbar instrumentation: a prospective study", J Neurosurg 87:397-402, (1997).

Zouridakis, et al., "A Concise Guide to Intraoperative Monitoring", Library of Congress card No. 00-046750, Chapters, p. 21, chapter 4, p. 58 and chapter 7 pp. 119-120.

Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.

Chapter 9, "Root Finding and Nonlinear Sets of Equations", Chapter 9:350-354, http://www.nr.com.

Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".

Ford et al., Electrical characteristics of peripheral nerve stimulators, implications for nerve localization, Dept. of Anesthesia, University of Cincinnati College of Medicine, Cincinnati, OH 45267, pp. 73-77.

Deletis et al., "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.

Urmey "Using the nerve stimulator for peripheral or plexus nerve blocks" Minerva Anesthesiology 2006; 72:467-71.

Butterworth et al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.

Calancie, et al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).

Calancie, et al., "Threshold-level repetitive transcranial electrical stimulation for intraoperative monitoring of central motor conduction", J. Neurosurg 95:161-168 (2001).

Calancie, et al., Stimulus-Evoked EMG Monitoring During Transpedicular Lumbosacral Spine Instrumentation, Initial Clinical Results, 19 (24):2780-2786 (1994).

Carl T. Brighton, "Clinical Orthopaedics and Related Research", Clinical Orthopaedics and related research No. 384, pp. 82-100 (2001).

International Search Report for PCT/US2019/063793, dated Feb. 19, 2020.

International Search Report for PCT/US2017/062559, dated Jan. 26, 2018.

* cited by examiner

Full Craniotomy used for conventional placement of grid electrode

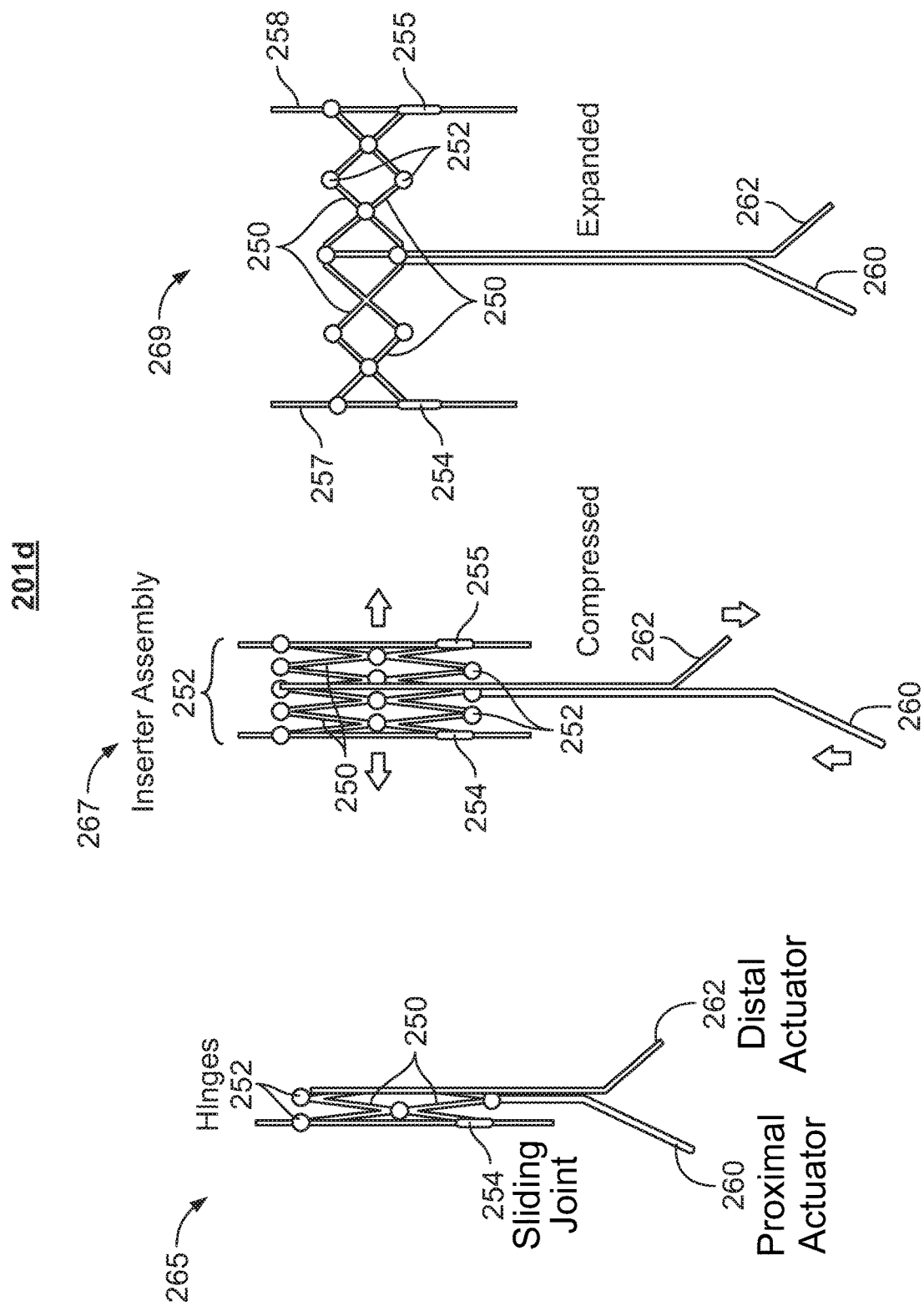

MINIMALLY INVASIVE TWO-DIMENSIONAL GRID ELECTRODE

CROSS-REFERENCE

The present application relies on U.S. Patent Provisional Application No. 62/732,654, filed on Sep. 18, 2018 and entitled "Minimally Invasive Two-Dimensional Grid Electrode", and U.S. Patent Provisional Application No. 62/767,504, filed on Nov. 14, 2018 and entitled "Method and System for Electrode Verification", for priority, both of which are incorporated herein by reference.

FIELD

The present specification is related generally to the field of electrodes. More specifically, the present specification is related to a compressible multi-contact electrode that can be inserted through an access hole via a surgical procedure, expanded to its full dimensions, verified as to position and location prior to completion of the surgical procedure, and preferably extracted via the same access hole.

BACKGROUND

Surgical treatment for epilepsy is being utilized more often when drug medical therapy fails to control the disease. Evaluation prior to surgery involves conducting direct brain recordings to verify that the epileptic focus is treatable. This type of evaluation is well understood by those of ordinary skill in the art.

Typically, hundreds of electrodes are needed to thoroughly map the brain. The electrodes employed may be in arrays, for example an 8×8 array with 64 contacts. To implant these electrode arrays, a section of skull is removed (skull flap) to allow placement of the electrodes, as shown in FIG. 1. Referring to FIG. 1, the electrodes are in a grid array 100 and are typically thin and flexible. Some electrodes or a portion of the electrode array 100 will be placed at the location of the skull flap, and other electrodes will be tucked between the skull and the brain over surfaces that are not directly exposed. To remove the electrode arrays, another surgical procedure is needed. The risks, costs and discomfort for these procedures are significant.

Other electrodes employed may be strip electrodes or needle-like depth electrodes. Strip electrodes may be inserted radially through burr holes, which are typically on the order of 2 cm in diameter. Depth electrodes may be inserted through small drill holes in the skull and removed without anesthesia.

Further, the placement of electrodes is important for interpreting electrode signals that are generated. The desired electrode locations are usually well defined and may be on the surface of the scalp, in or on the brain, or at some other location on the body. Depth electrodes and grid electrodes consist of multiple electrodes in a matrix, where the expected geometric relation of each input to all other inputs within the matrix is known. In complex cases with multiple grids or multiple depth electrodes, the locations of each individual or group of electrodes is either part of the surgical planning or is noted during the surgery. A placement error will lead to either confusion because the testing results do not make sense or worse—a mistaken conclusion that can affect treatment and outcome.

What is needed is a compressible grid electrode that can be compressed, folded, or otherwise modified in shape to allow for insertion and that is configured to subsequently unfolded when in the proper location. What is also needed is a folding grid electrode that is configured to be inserted into a relatively small access hole that can be expanded to its full dimension, that can be verified as to position and location prior to completion of the surgical procedure, and that can be extracted via the same access hole.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a system for deploying an electrode array at a target location within a patient's cranium through a hole formed in the patient's cranium, the system comprising: a substrate; an array of electrodes attached to the substrate; an inserter attached to the substrate, wherein the inserter, the substrate, and the array of electrodes are configured in a first compressed state and wherein the inserter is configured to expand from the first compressed state to a second uncompressed state; and a cannula configured to accommodate the inserter, the substrate and the array of electrodes in the first compressed state and configured to release the inserter, the substrate and the array of electrodes through the hole and within the patient's cranium at the target location.

Optionally, in the first compressed state, the substrate and array of electrodes have a width that is less than a width of the substrate and array of electrodes in the second uncompressed state.

Optionally, the array of electrodes comprises a plurality of contacts having associated lead wires, and wherein each of said lead wires are connected to a terminal on an electrical device.

Optionally, the system further comprises an actuator coupled to the inserter. Optionally, the actuator is configured to be accessible outside the patient's cranium and further configured such that, when a force is applied to the actuator, in a first direction, the inserter expands, thereby causing the inserter, the substrate, and the array of electrodes to be in the second uncompressed state. Optionally, the actuator is configured to be accessible outside the patient's cranium and further configured such that, when a force is applied to the actuator, in a second direction, the inserter compresses, thereby causing the inserter, the substrate, and the array of electrodes to be in the first compressed state.

Optionally, the inserter comprises at least a first spring element and a second spring element, wherein a distal end of the first spring element is attached to a first edge of the substrate, wherein a distal end of the second spring element is attached to a second edge of the substrate, and wherein the first edge opposes the second edge. Optionally, a proximal end of the first spring element and a proximal end of the second spring element are connected to a common member.

Optionally, the inserter comprises a multi-segmented cantilever coupled to a first and a second actuator. Optionally, the multi-segmented cantilever is configured to expand when the first actuator is pulled in a first direction and the second actuator is pushed in an opposing second direction.

Optionally, the substrate has a tapered proximal portion configured to facilitate ease of extraction of the substrate through the hole.

Optionally, the cannula includes a mark to facilitate a proper orientation of a contact surface of the array of electrodes during release of the inserter, the substrate and the array of electrodes.

Optionally, the cannula has an ovoid cross-section and is curved along its length.

Optionally, the cannula includes a port configured to provide compressed gas to generate a brain-cranium gap for inserting the cannula through the hole.

Optionally, the cannula further accommodates a front-pointing viewing element and at least one illuminator.

The present specification also discloses a method of deploying an electrode array at a target location within a patient's cranium through a hole formed in the patient's cranium, the method comprising: obtaining an electrode array system, wherein the electrode array system comprises a cannula having a lumen, a substrate, an array of electrodes attached to the substrate, and an inserter attached to the substrate, wherein the substrate, the array of electrodes, and the inserter are positioned in the lumen in a first compressed state; inserting the cannula through the hole; sliding the cannula backwards while positioning the inserter, the substrate, and the array of electrodes at the target location; and causing the inserter, the substrate and the array of electrodes to transition from the first compressed state to a second uncompressed state at the target location.

Optionally, in the first compressed state, the substrate and array of electrodes have a width that is less than a width of the substrate and the array of electrodes in the second uncompressed state.

Optionally, the array of electrodes comprises a plurality of contacts having associated lead wires and wherein each of said lead wires are connected to a terminal on an electrical device.

Optionally, the method further comprises causing the inserter, the substrate and the array of electrodes to transition from the first compressed state to the second uncompressed state by moving an actuator attached to the inserter. Optionally, the actuator is configured to be accessible outside the patient's cranium and further configured such that, when a force is applied to the actuator, in a first direction, the inserter expands, thereby causing the inserter, the substrate, and the array of electrodes to be in the second uncompressed state. Optionally, the actuator is configured to be accessible outside the patient's cranium and further configured such that, when a force is applied to the actuator, in a second direction, the inserter compresses, thereby causing the inserter, the substrate, and the array of electrodes to be in the first compressed state.

Optionally, the inserter comprises at least a first spring element and a second spring element, wherein a distal end of the first spring element is attached to a first edge of the substrate, wherein a distal end of the second spring element is attached to a second edge of the substrate, and wherein the first edge opposes the second edge. Optionally, a proximal end of the first spring element and a proximal end of the second spring element are connected to a common member.

Optionally, the inserter comprises a multi-segmented cantilever coupled to an actuator. Optionally, the multi-segmented cantilever is configured to expand when the actuator is pulled in a first direction and configured to contract when the actuator is pulled in a second direction.

Optionally, the method further comprises causing the inserter, the substrate and the array of electrodes to transition from the second uncompressed state to the first uncompressed state at the target location. Optionally, the inserter, the substrate and the array of electrodes transitions from the second uncompressed state to the first uncompressed state by moving an actuator in physical communication with the inserter. Optionally, the method further comprises removing the cannula and the inserter through the hole. Optionally, the method further comprises extracting the array of electrodes through the hole.

Optionally, the method further comprises verifying a physical position of at least one of the inserter, the substrate or the array of electrodes within the patient's cranium.

The present specification also discloses a method of deploying an electrode array at a target location onto a patient's cortex through a burr hole formed on the patient's cranium, the method comprising: inserting a cannula through said burr hole, said cannula accommodating an inserter and an array of electrodes, wherein said inserter and array of electrodes are in a first state; sliding the cannula backwards while positioning said inserter and array of electrodes in said first state at said target location; causing said array of electrodes to be in a second state at said target location; and verifying said positioning of said inserter and array of electrodes at said target location.

Optionally, the method further comprises removing the cannula and the inserter through the burr hole. Optionally, the method further comprises extracting the array of electrodes through the burr hole.

Optionally, in said first state, the inserter and array of electrodes are compressed.

Optionally, in said second state, the array of electrodes is expanded.

The present specification also discloses a system for deploying an electrode array at a target location onto a patient's cortex through a burr hole formed on the patient's cranium, the system comprising: an array of electrodes formed on a substrate; an inserter attached to the array of electrodes, wherein the inserter and array of electrodes are configured into a first state; and a cannula, wherein the cannula accommodates the inserter and array of electrodes in said first state, and wherein the cannula is inserted through the burr hole to deploy the array of electrodes at the target location in a second state.

Optionally, in said first state, the inserter and array of electrodes are compressed.

Optionally, in said second state, the array of electrodes is expanded.

Optionally, the array of electrodes comprises a plurality of contacts having associated lead wires, wherein said lead wires are bundled into at least one pigtail.

Optionally, an actuator is coupled to the inserter. Optionally, application of a force on the actuator in a direction causes the inserter to be expanded, thereby causing the array of electrodes to be in said second state.

Optionally, the cannula and the inserter are removed from the burr hole after the array of electrodes is deployed in said second state.

Optionally, the array of electrodes is removed through the burr hole using said at least one pigtail.

Optionally, the inserter comprises a multi-segmented cantilever coupled to an actuator.

The present specification also discloses a method of deploying an electrode array at a target location onto a patient's cortex through a burr hole formed on the patient's cranium, the method comprising: inserting a cannula through said burr hole, said cannula accommodating an inserter and an array of electrodes, wherein said inserter and array of electrodes are in a first state; and sliding the cannula backwards while positioning said inserter and array of electrodes in said first state at said target location.

Optionally, the method further comprises causing said inserter and array of electrodes to be in a second state at said target location.

Optionally, said second state is caused by activating an actuator coupled to said inserter.

Optionally, the method further comprises verifying said positioning of said inserter and array of electrodes at said target location.

Optionally, the method further comprises removing the cannula and the inserter through the burr hole.

Optionally, the method further comprises extracting the array of electrodes through the burr hole.

The present specification also discloses a method of deploying an electrode array at a target location onto a patient's cortex through a burr hole formed on the patient's cranium, the method comprising: inserting a cannula through said burr hole, said cannula accommodating an inserter and an array of electrodes, wherein said inserter and array of electrodes are in a first state; sliding the cannula backwards while positioning said inserter and array of electrodes in said first state at said target location; causing said array of electrodes to be in a second state at said target location; and verifying said positioning of said inserter and array of electrodes at said target location.

Optionally, the method further comprises removing the cannula and the inserter through the burr hole.

Optionally, the method further comprises extracting the array of electrodes through the burr hole.

Optionally, in said first state, the inserter and array of electrodes are compressed.

Optionally, in said second state, the array of electrodes is expanded.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 2D shows an inserter configured in the form of a scissors jack mechanism, in accordance with some embodiments of the present specification;

DETAILED DESCRIPTION

Figure 1:
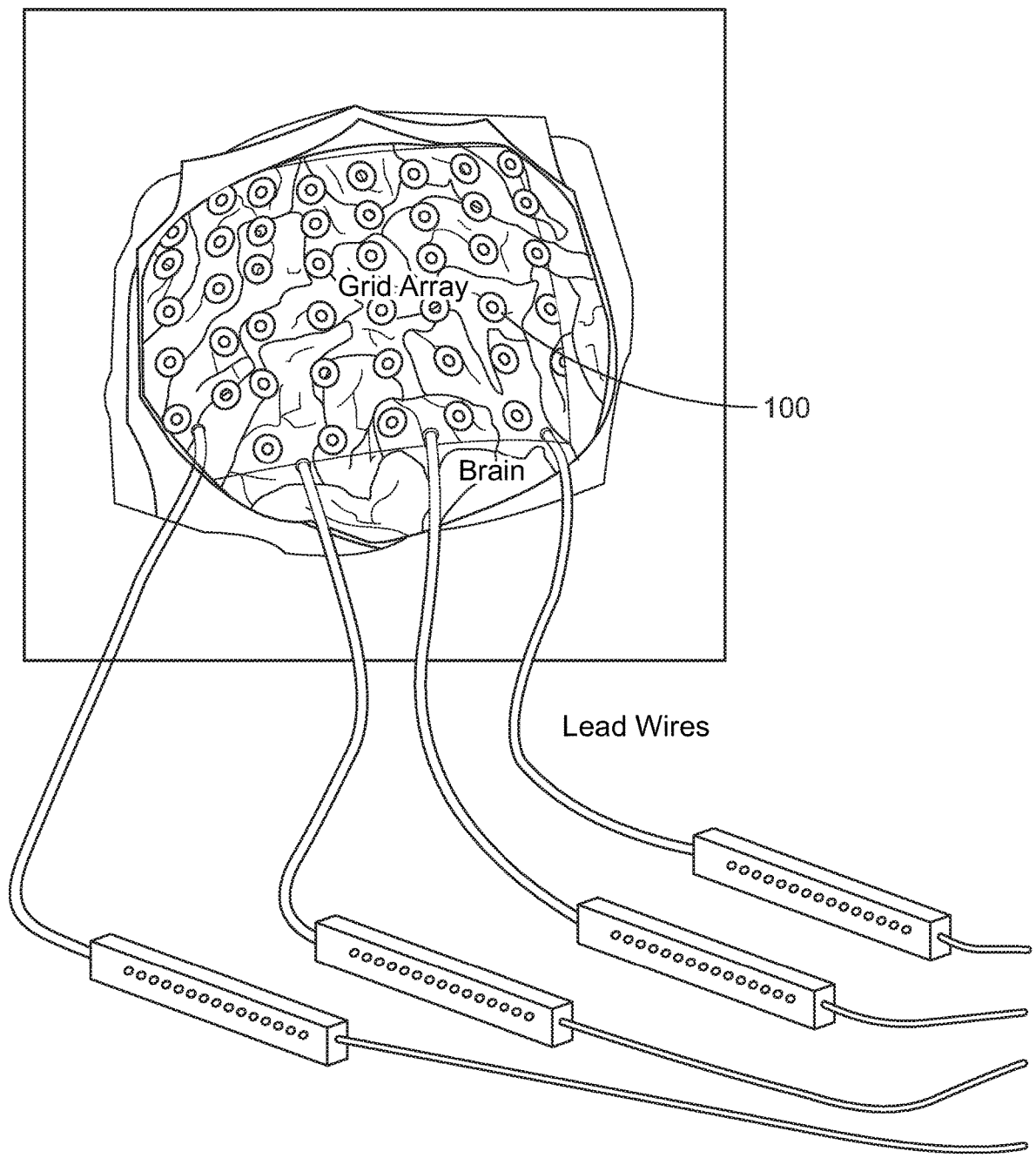
FIG. 1 is an illustration of a conventional technique for applying grid electrodes.

The term 'user' is used interchangeably to refer to a surgeon, neuro-physician, neuro-surgeon, neuro-physiologist, technician or operator of an electroencephalogram or electroencephalography (EEG) system and/or other patient-care personnel or staff.

A "computing device" is at least one of a cellular phone, PDA, smart phone, tablet computing device, patient monitor, custom kiosk, or other computing device configured to execute programmatic instructions. It should further be appreciated that each device and monitoring system may have wireless and wired receivers and transmitters capable of sending and transmitting data. Each "computing device" may be coupled to at least one display, which displays information about the patient parameters and the functioning of the system, by means of a graphical user interface (GUI). The GUI also presents various menus that allow users to configure settings according to their requirements. The system further comprises at least one processor to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium. In addition, the software comprised of a plurality of programmatic instructions for performing the processes described herein may be implemented by a computer processor capable of processing programmatic instructions and a memory capable of storing programmatic instructions.

"Electrode" refers to a conductor used to establish electrical contact with a nonmetallic part of a circuit. EEG electrodes are small metal discs usually made of stainless steel, tin, gold or silver covered with a silver chloride coating. They are typically placed on the scalp on predetermined locations. "Depth electrodes" are made of thin wires, are configured to record seizures which may start deep in the brain, and are typically inserted into the brain parenchyma. "Strip and grid electrodes" are conductors that are positioned, implanted or embedded within a thin sheet of plastic and are typically configured to be placed on a surface of the brain.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

The present specification is directed towards electrodes and inserters, together referred to as an "electrode system", configured to allow for insertion of a compressible grid electrode, in a compressed configuration, through a relatively small hole, which can then be expanded to position an array of contacts over the surface of the brain. In some embodiments, the hole is dime-sized. In some embodiments, a diameter of the hole ranges between 2 mm and 30 mm, preferably 10 mm to 20 mm, and any numerical increment therein. The system can then use an electrode location system to verify that the grid electrode is properly positioned during the surgery. The grid electrode may be removed without additional surgery in an antiseptic environment.

Figure 2A:
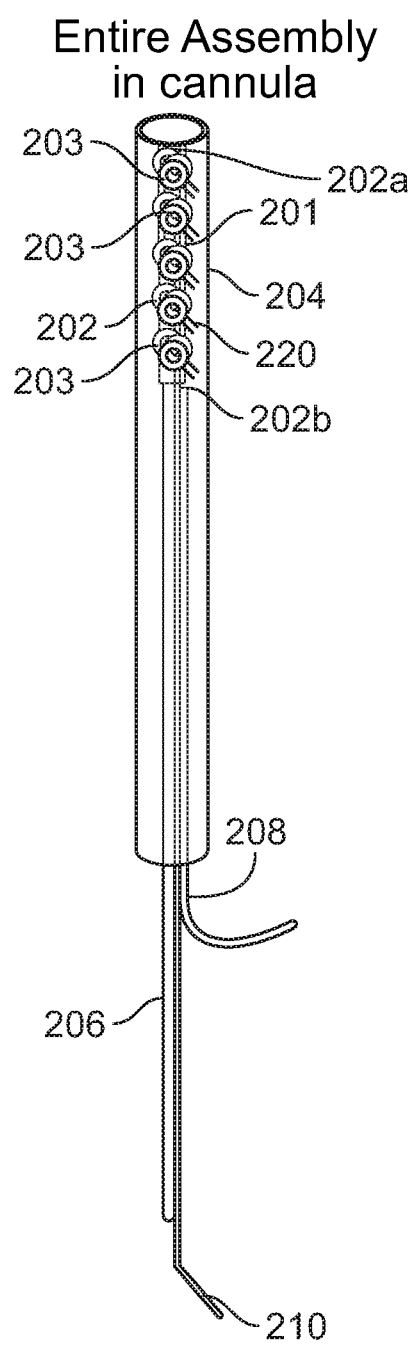
FIG. 2A is an illustration of an electrode system, in compressed form and housed in a cannula, in accordance with some embodiments of the present specification.

FIG. 2A illustrates an assembly of an electrode system 200, with electrode array 202 in compressed form and housed in a cannula 204, in accordance with some embodiments of the present specification. The electrode system 200 comprises an inserter 201 attached to the electrode array 202. The electrode system 200 is in compressed form and contained within the cannula 204, wherein the cannula 204 is stiff enough to be inserted into a desired location and depth of a patient's skull or cranium. In embodiments, the electrode array 202 comprises a distal end 202a and a proximal end 202b.

Figure 2B:
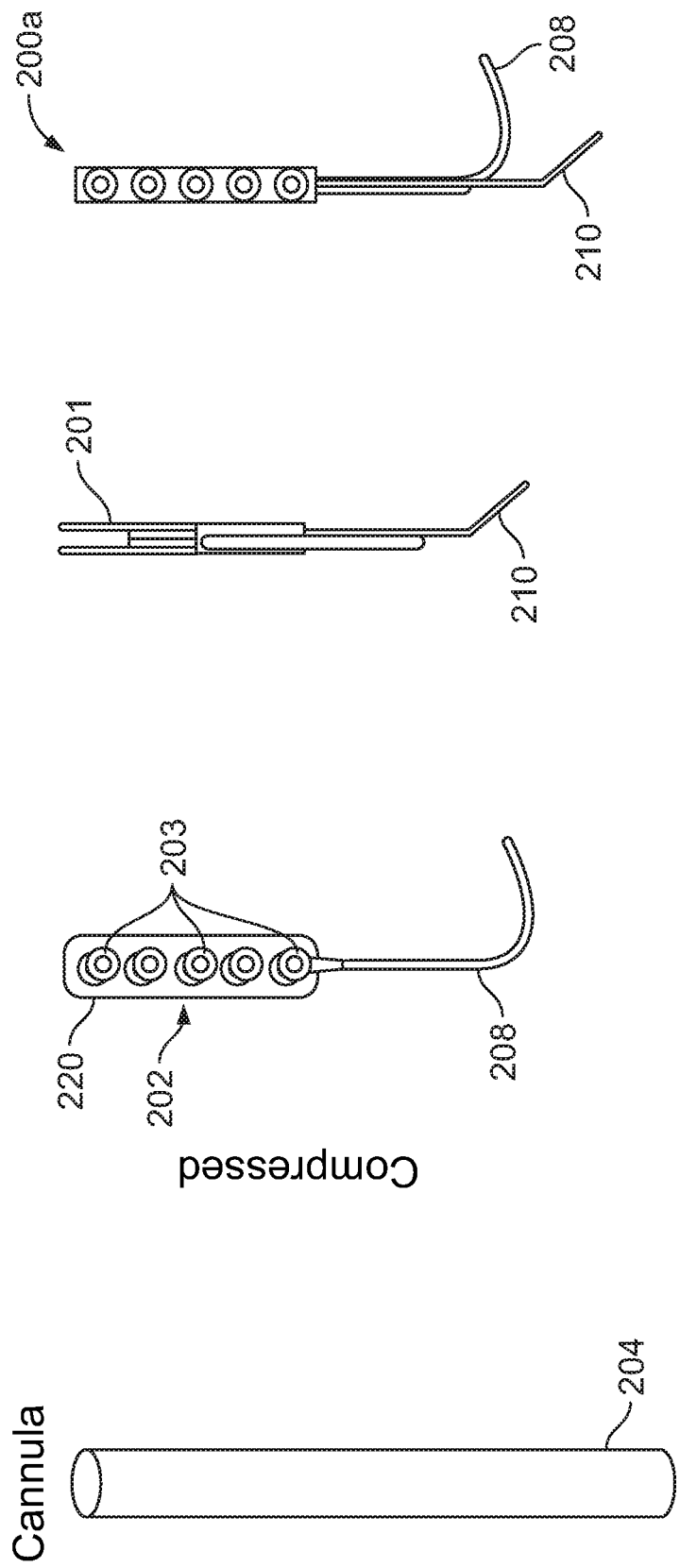
FIG. 2B is an illustration of an electrode system, in compressed form and removed from a cannula, in accordance with some embodiments of the present specification.
Figure 2C:
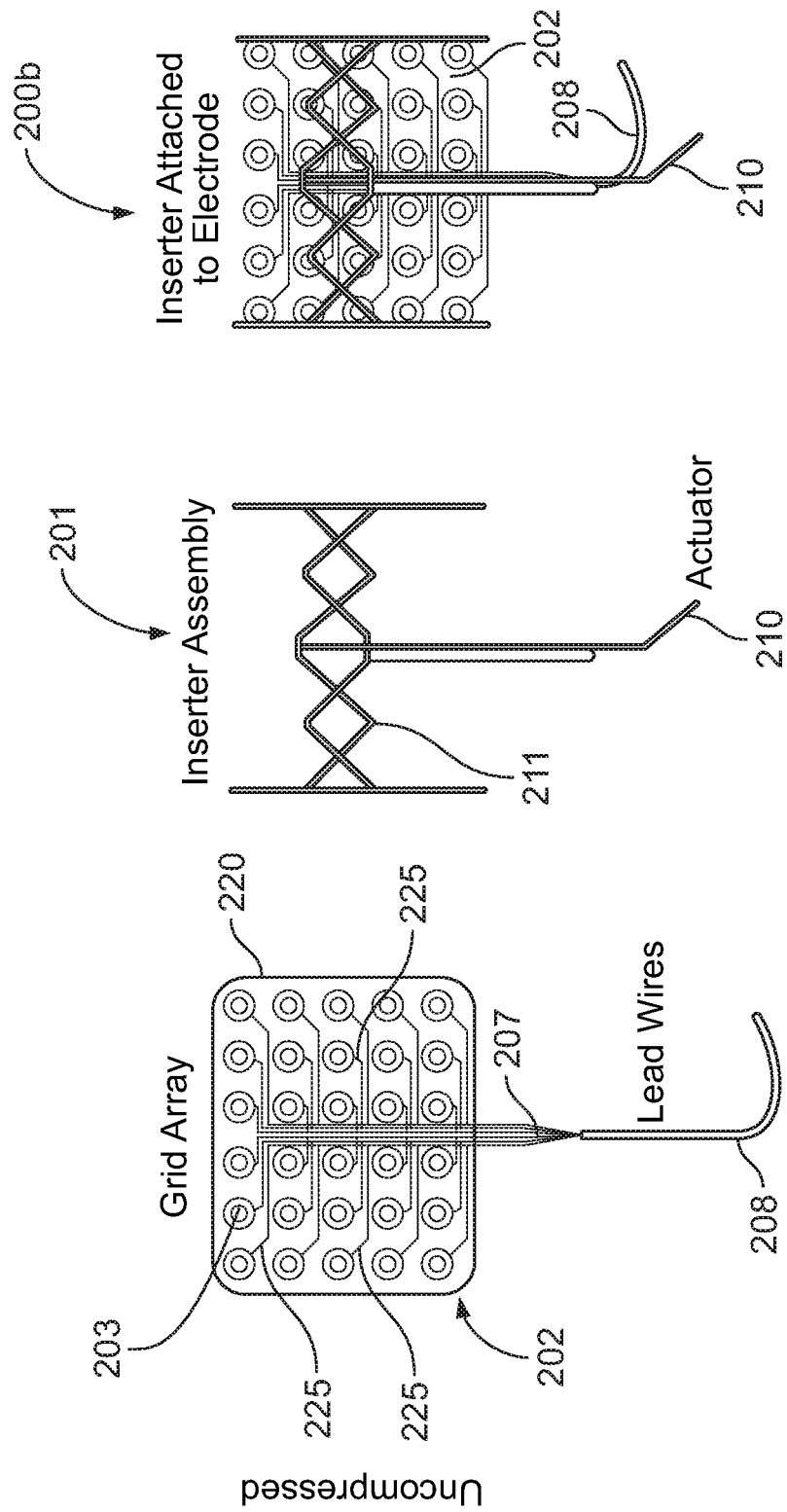
FIG. 2C is an illustration of the electrode system of FIGS. 2A and 2B, in uncompressed or expanded form, in accordance with some embodiments of the present specification.

In an embodiment, the electrode array 202 is a grid electrode and consists of an array of contacts 203, each of which has a lead wire 207 (visible in FIG. 2C). The lead wires 207 are bundled into one or more pigtails 208 and terminated in a multi-contact connector. A pigtail is defined as a short length of wire that connects, at one end, to a terminal on an electrical or computing device and, at the other end to circuit wires. Within or alongside the compressed electrode array 202 is a guide wire 206. In an alternate configuration, a plunger may follow the lead wires 207 to the proximal end 202b of the compressed electrode array 202. Operationally, after the cannula 204 has been inserted into a patient's skull, the cannula is pulled back to thereby release the compressed electrode array 202 at the desired location. The guide wire 206 or the plunger is then used to keep the electrode array 202 at the desired location and depth. The electrode system 200 also includes, in some embodiments, an actuator 210 described in greater detail below.

FIG. 2B is an illustration of the electrode system 200 of FIG. 2A, with electrode array 202 in compressed form and removed from the cannula 204, in accordance with some embodiments of the present specification. The electrode array 202 is shown in a compressed configuration with the array of contacts 203 and the lead wires (or electrode leads) 207 bundled into at least one pigtail 208. The electrode leads are flexible and resist breakage when the electrode array 202 is compressed and uncompressed.

In embodiments, the electrode array 202 is attached or coupled to a substrate 220 having length and/or width dimensions of 2 cm to 15 cm in an uncompressed form. The substrate 220 of the electrode array 202 is of sufficient strength and flexibility so that the array 202 will not fragment during insertion or removal. In some embodiments, if necessary, reinforcing filaments can be added to the substrate which will effectively distribute the forces that come into play during compression and release of the electrode array 202. In embodiments, the substrate is biocompatible for temporary implantation and can be sterilized. In various embodiments, the substrate 220 is made of flexible biocompatible material such as silicone rubber and with conductive contacts as are currently used for grid electrodes such as stainless steel, platinum or carbon. The geometry can be variable both in size and shape as is currently supported by invasively placed cortical grid electrodes. The contacts may also be placed asymmetrically to accommodate optimal spring positions and to allow ease of placement and removal.

In various embodiments, the electrode array 202 is compressed into a plurality of configurations such as, but not limited to, a first configuration wherein the array 202 is rolled up, a second configuration wherein the array 202 is folded in an accordion-like manner, a third configuration wherein the array 202 is compressed in a serpentine manner, a fourth configuration wherein the array 202 is squeezed in a tube-like manner or in other ways or configurations that combine or are different from these four exemplary configurations.

Also shown in FIG. 2B is the inserter 201 in compressed form along with an actuator 210. A compressed assembly 200a of the inserter 201 and the electrode array 202 is also shown. In the compressed form, the inserter 201 has dimensions of 2 cm to 15 cm long and less than 1 cm in width. In various embodiments, the inserter 201 is attached or coupled to the electrode array 202 and/or the substrate 220 using any attachment means known in the art. In some embodiments, in a compressed state, the substrate 220, in combination with the electrodes/contacts 203, the inserter 201 and the lead wires 207, have dimensions that are less than the dimensions of the substrate, electrode/contacts, and lead wires in an uncompressed state.

FIG. 2C is an illustration of the electrode system 200 of FIGS. 2A and 2B, in uncompressed or expanded form, in accordance with some embodiments of the present specification. As described earlier, the grid electrode array 202 consists of an array of contacts 203, each of which has a lead wire 207. The lead wires 207 are bundled into one or more pigtails 208 and terminated in a multi-contact connector. The pigtails 208 pass through the patient's skull and skin and the connector is external to the patient. In some embodiments, the grid electrode array 202 may be fabricated on the substrate 220 which is thin and flexible and which conforms to the surface of the patient's brain when applied, and which can be compressed or folded into a tube-like structure for insertion.

An uncompressed or unfurled configuration 200b of the inserter 201 and the electrode array 202 is also shown. The unfurling of the electrode array 202 requires it to roll across or slide across the surface of the patient's brain. In embodiments, this is accomplished in a plurality of ways depending on the compression method and the shape or configuration of the final compressed grid array 202. In various embodiments, a scissors action, a fluid filled hydraulic system built into the grid array 202, a multi-segmented cantilevered action, or a spring which is gradually released as the cannula 204 is retracted is used to accomplish the unfurling. In other embodiments, the grid 202 comprises a shape-memory material that expands once the cannula 204 is retracted from the compressed assembly of the electrode array 202 and inserter 201. In some embodiments, a combination of these unfurling systems is used.

The inserter 201 is also shown in uncompressed form in the FIG. 2C, which employs a mechanical actuator 210 to unfurl the compressed electrode system 200a (shown in FIG. 2B) into an uncompressed state 200b for placement on the surface of a patient's brain, in accordance with some embodiments of the present specification. In some embodiments, as shown in FIG. 2C, the actuator 210 is coupled to a collapsible as well as expandable structure 211 (for example, a multi-segmented cantilever). In some embodiments, a force applied on the actuator 210 in a first direction causes the structure 211 to expand (thereby causing the attached electrode array 202 to also unfurl) while a force applied on the actuator 210 in a second direction (opposite to the first direction) causes the structure 211 to collapse or compress.

FIG. 2D shows an exemplary inserter 201d configured in the form of a multi-segmented cantilever or scissors jack mechanism, in accordance with some embodiments of the present specification. Configuration 265 shows the inserter 201d in a fully compressed state, configuration 267 shows the inserter 201d in a partially expanded state while configuration 269 shows the inserter 201d in a fully expanded state. The scissors jack mechanism of the inserter 201d comprises a plurality of segments 250 coupled together via a plurality of hinges 252 that allow flexible expansion or compression of the segments 250. First and second sliding joints 254, 255 enable portions of the coupled segments 250 to slide up or down along first and second bars 257, 258 during expansion or compression of the segments 250, respectively. The inserter 201d also comprises a proximal actuator 260 and a distal actuator 262 to enable modulation of the inserter 201d into expanded or compressed states. During operation, a user pulls the distal actuator 262 down (or holds stationary) and pushes the proximal actuator 260 up thereby applying opposing forces to the proximal and distal hinges 252 and expanding the scissors jack mechanism laterally.

Figure 3:
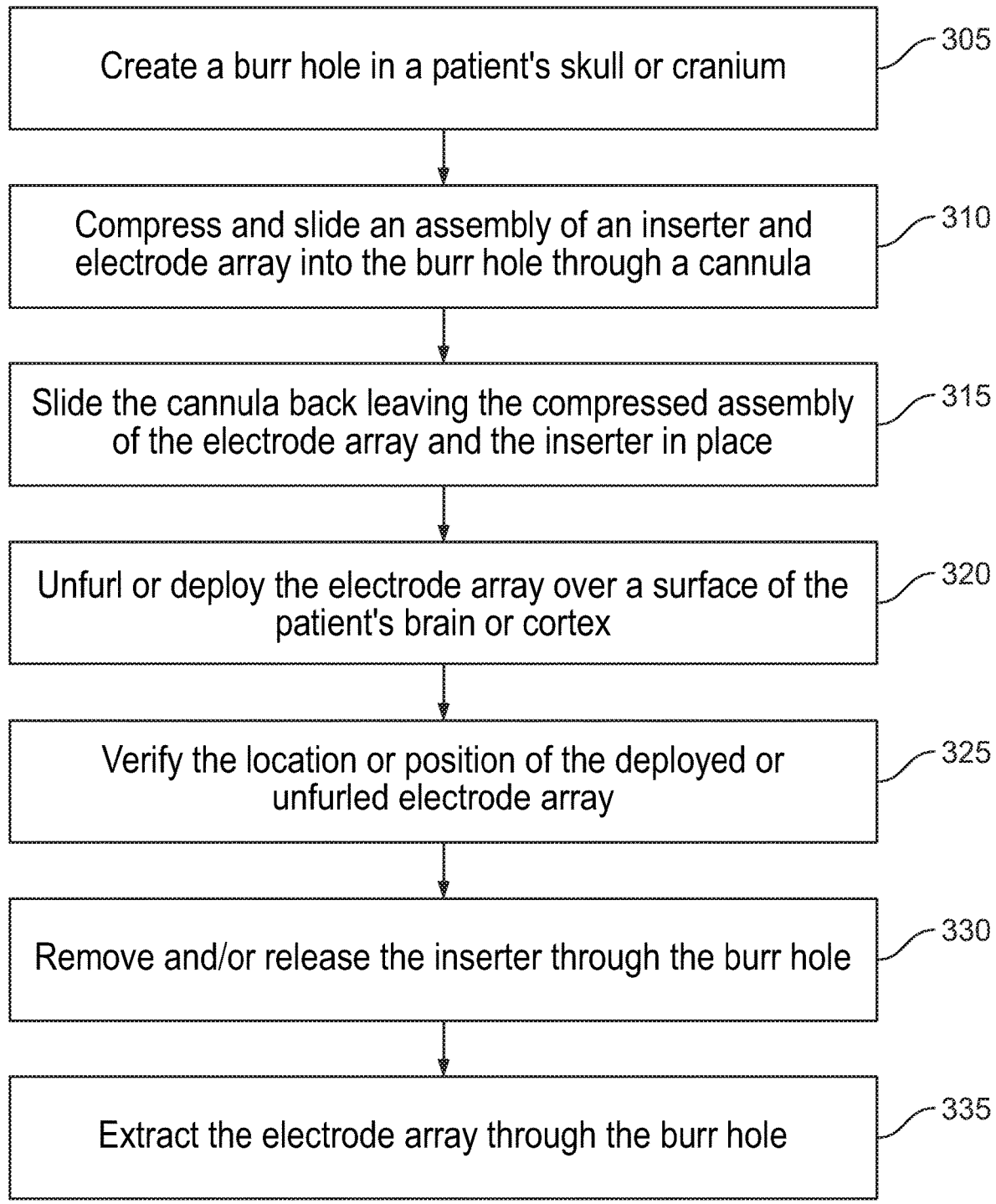
FIG. 3 is a flow chart describing exemplary steps for inserting, expanding, verifying, and extracting the electrode system, in accordance with some embodiments of the present specification.

FIG. 3 is a flow chart describing exemplary steps for inserting, expanding, verifying, and extracting the electrode system, in accordance with some embodiments of the present specification. At step 305, an insertion, access or burr hole is formed or created in a patient's skull or cranium at a desired location and of a desired depth so as to enable access to a surface of the patient's brain or cortex. At step 310, an assembly of an inserter attached to an electrode array is compressed and slid or inserted into the access or burr hole through a cannula. At step 315, the cannula is slid back leaving the compressed assembly of the electrode array and the inserter in place.

At step 320, the electrode array is uncompressed, unfurled, deployed or expanded over the surface of the patient's brain or cortex and at the desired location or position. In some embodiments, the electrode array is unfurled by applying a force, in a direction, to an actuator coupled to the inserter wherein the inserter is a multi-segmented cantilever. In some embodiments, the electrode array is unfurled by a scissors action of the actuator or inserter. In some embodiments, the inserter is a hydraulically actuated system built into the electrode array wherein actuation of the hydraulic pressure causes the electrode array to unfurl. In some embodiments, the inserter is embodied as a spring that is gradually released as the cannula is retracted. In some embodiments, the inserter and/or the grid electrode array comprises a shape-memory material that expands passively causing the electrode array to unfurl.

At step 325, the location or position of the deployed or unfurled electrode array is verified to ensure that the location or position is indeed the intended, targeted or desired position. At step 330, the inserter is removed and/or released through the burr hole. In some embodiments, the inserter is a hydraulically actuated system wherein the associated hydraulic pressure is released for removal of the inserter. Finally when desired, at step 335, the electrode array is removed or extracted through the burr hole by teasing it out using at least one pigtail of the electrode array. In embodiments, the flexible substrate of the electrode array will collapse in on itself and exit via the insertion path and insertion or burr hole.

Figure 4:
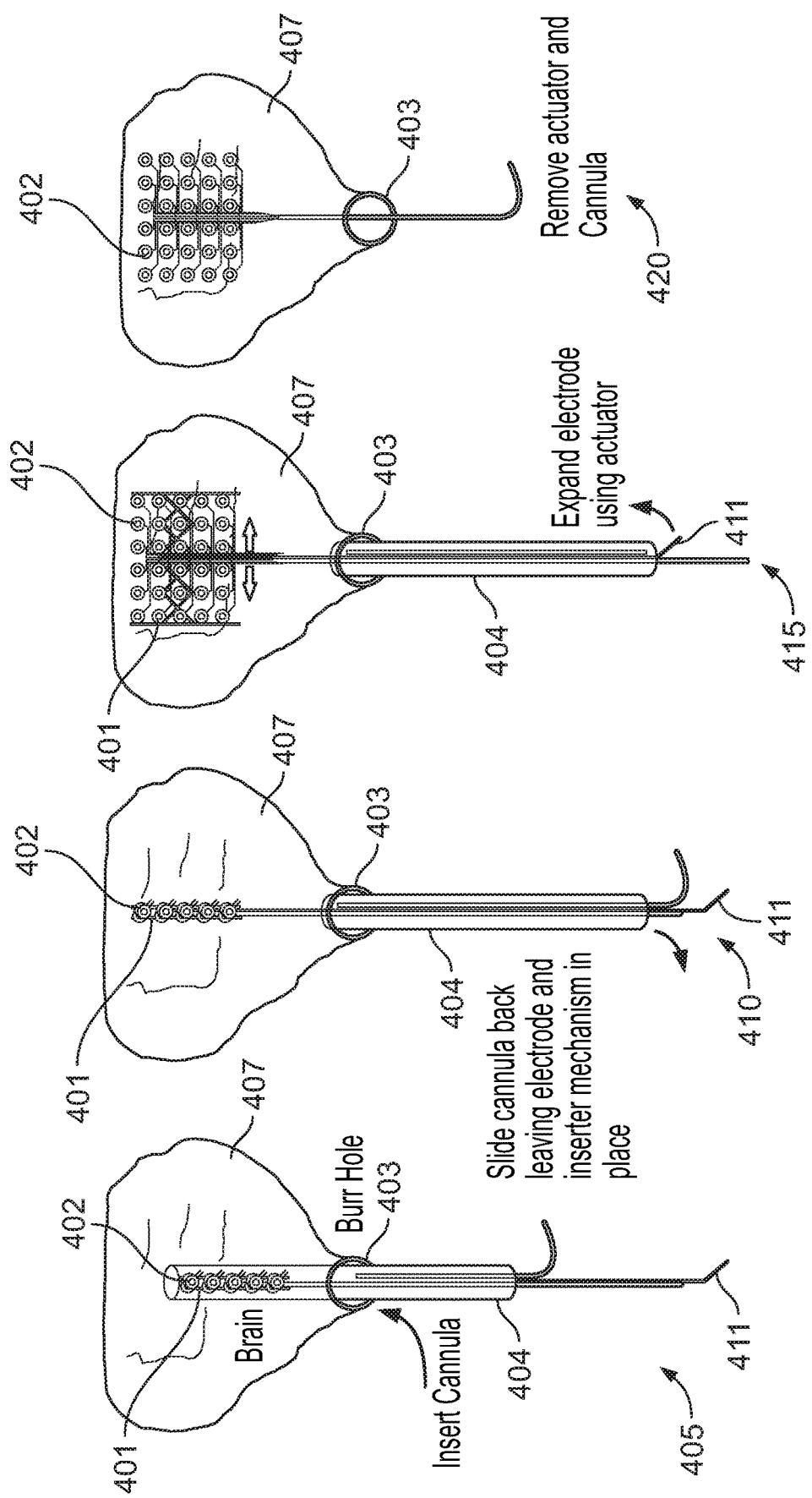
FIG. 4 illustrates exemplary steps for inserting the electrode system into a burr hole, in accordance with some embodiments of the present specification.

FIG. 4 illustrates exemplary steps for inserting the electrode system into a burr hole, in accordance with some embodiments of the present specification. At step 405, a cannula 404, comprising a compressed assembly of an inserter 401 attached to an electrode array 402, is inserted into a burr hole 403 formed in the cranium of a patient. At step 410, the cannula 404 is slid back, through the burr hole 403, leaving the compressed assembly of the inserter 401 and the electrode array 402 in position at a desired or target site on the patient's brain or cortex 407. At step 415, the electrode array 402 is deployed, uncompressed or unfurled by activating an actuator 411 coupled to the inserter 401. Finally, after deployment, at step 420 the inserter 401 and the cannula 404 are removed through the burr hole 403, leaving the electrode array 402 deployed on the patient's brain or cortex 407.

Figure 5:
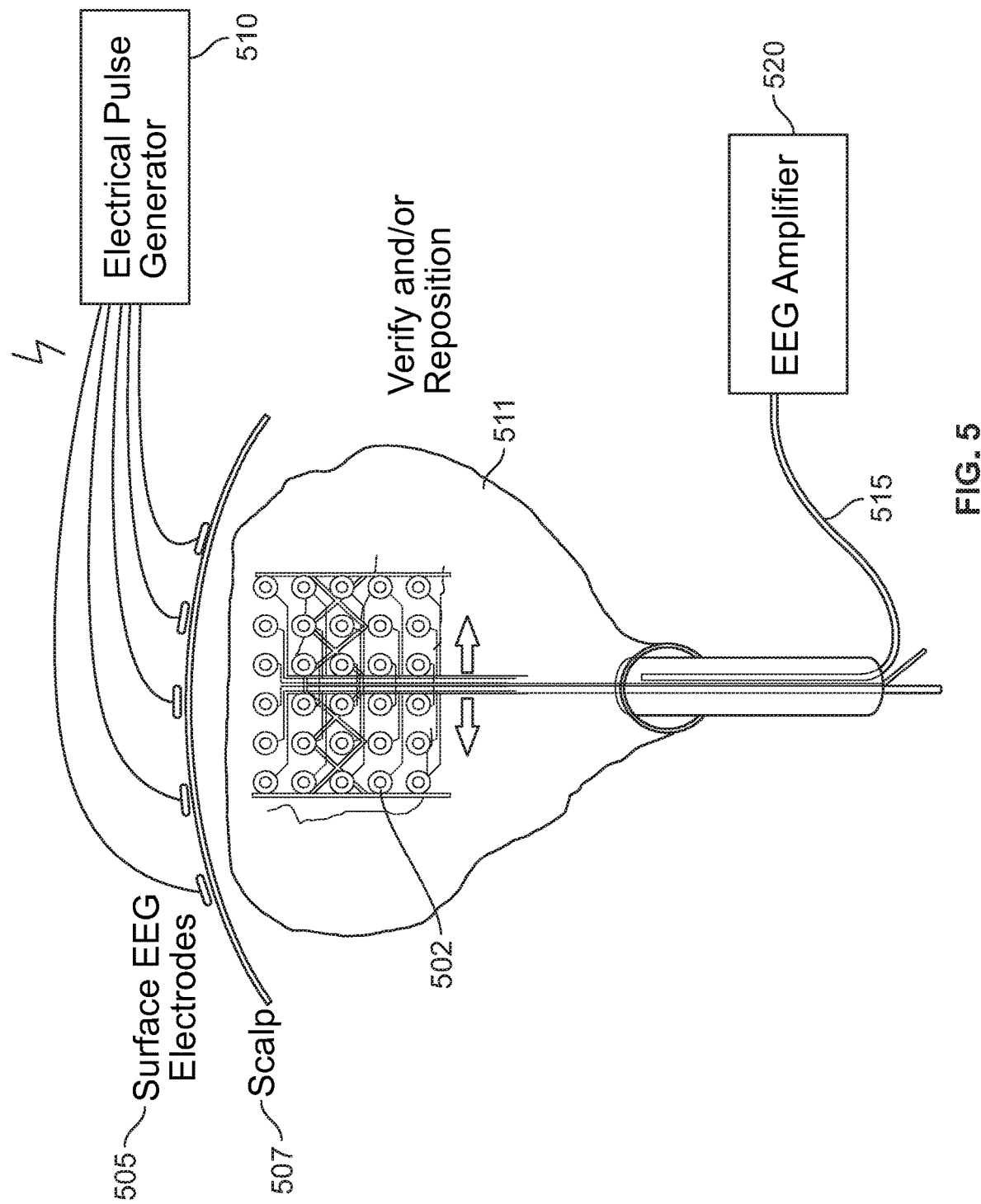
FIG. 5 illustrates exemplary steps for verifying electrode placement using excitation and field measurements, in accordance with some embodiments of the present specification.

FIG. 5 illustrates exemplary steps for verifying electrode placement using excitation and field measurements, in accordance with some embodiments of the present specification. For verification, a plurality of surface electrodes 505 are placed on a patient's scalp 507 such that the surface electrodes 505 are over the expected, intended, desired or target location where the electrode array 502 is supposed to have been implanted and deployed over the surface of the patient's brain or cortex 511. In other words, the surface electrodes 505 are located directly over the electrode array 502 such that they overlap or are mutually parallel with the patient's skull in between. Lead wires from the electrode array 502 are bundled into at least one pigtail 515 and are in electrical communication with an EEG amplifier 520. The surface electrodes 505 are in electrical communication with an electrical pulse generator 510 that causes pulsed electric field to be generated across the plurality of surface electrodes 505.

The pulsed electric field generated across the plurality of surface electrodes 505 is detected as a signal by each implanted grid electrode (of the electrode array 502). The location of each grid electrode is calculated from such signal using an inverse localization and statistical comparison to an expected, intended, desired or target location.

Figure 6A:
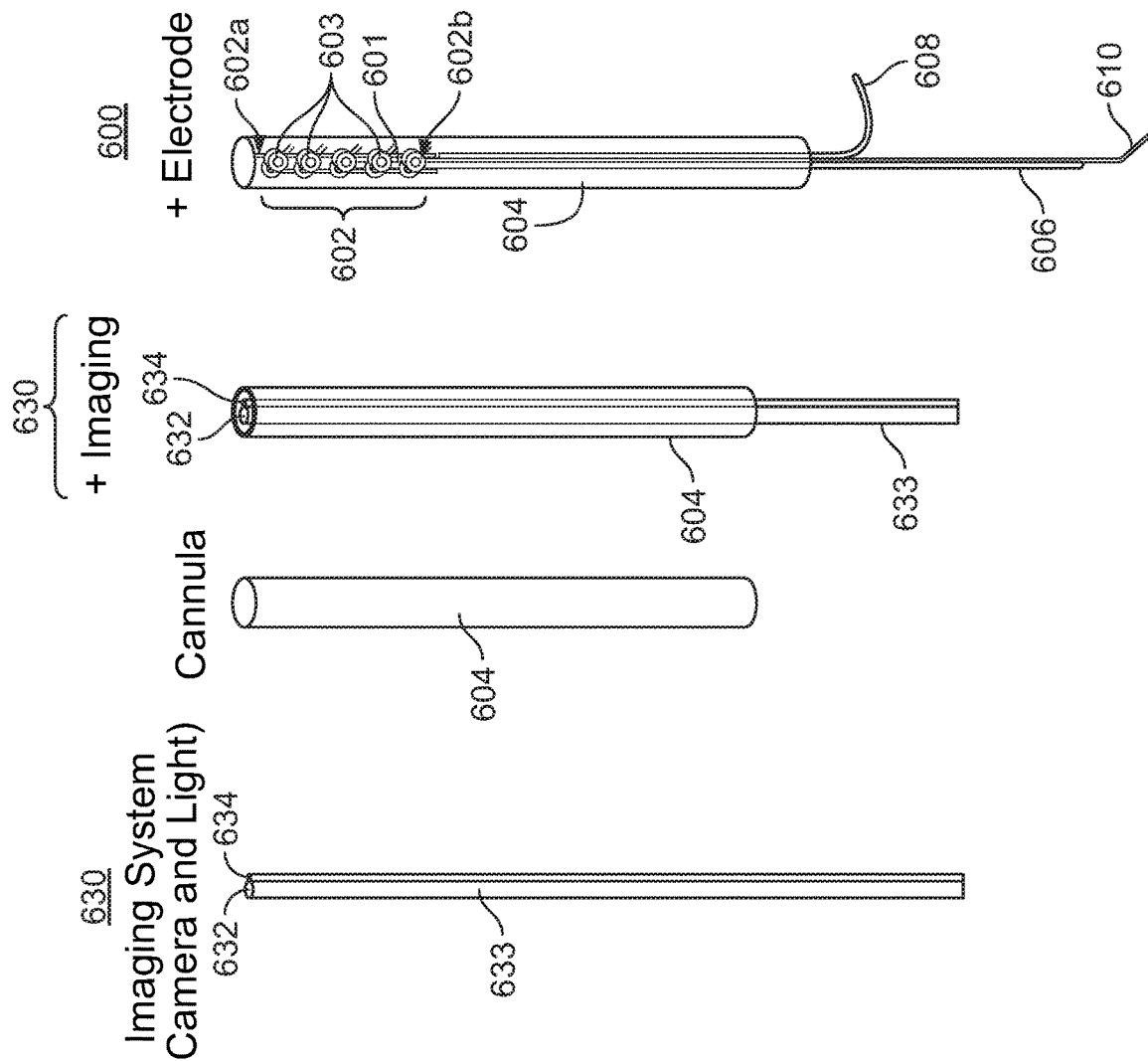
FIG. 6A illustrates an assembly of an electrode system in compressed form and housed in a cannula along with a visualization or imaging system, in accordance with some embodiments of the present specification.

FIG. 6A illustrates an assembly of an electrode system 600 in compressed form and housed in a cannula 604 along with a visualization or imaging system 630, in accordance with some embodiments of the present specification. The electrode system 600 comprises an inserter 601 attached to an electrode array 602. The electrode system 600 is in compressed form and contained within the cannula 604, wherein the cannula 604 is stiff enough to be inserted into a desired location and depth of a patient's skull or cranium. In embodiments, the electrode array 602 comprises a distal end 602a and a proximal end 602b.

Figure 6B:
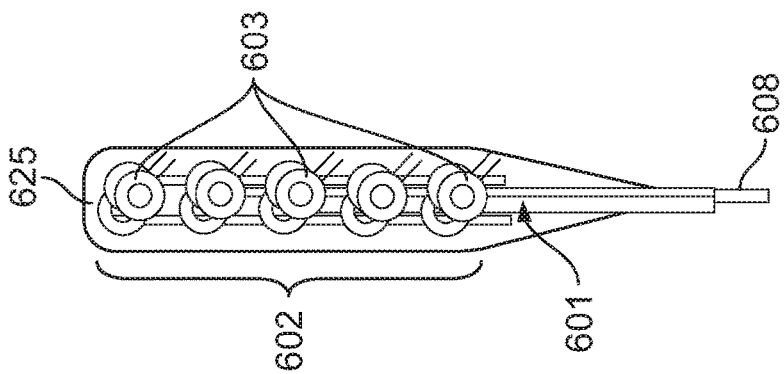
FIG. 6B is an illustration of the electrode system of FIG. 6A in compressed form and removed from the cannula, in accordance with some embodiments of the present specification.
Figure 6B:
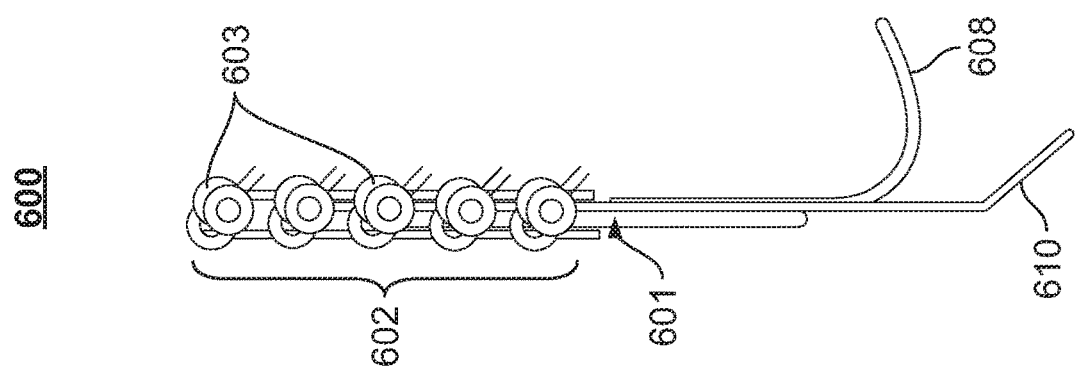
Figure 6B:
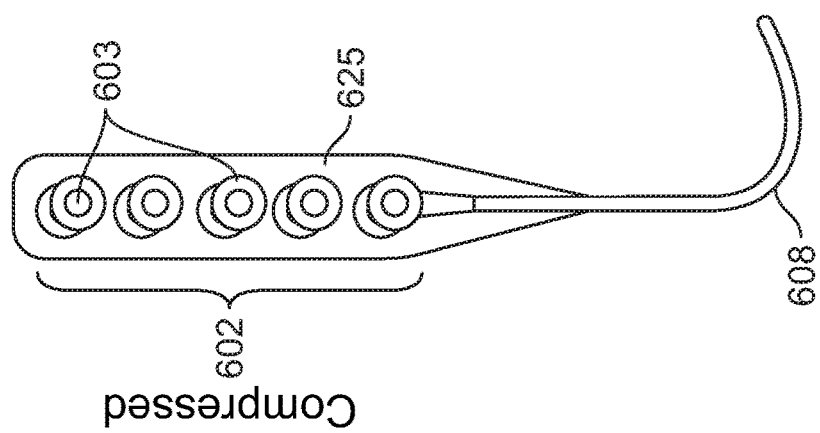
Figure 6C:
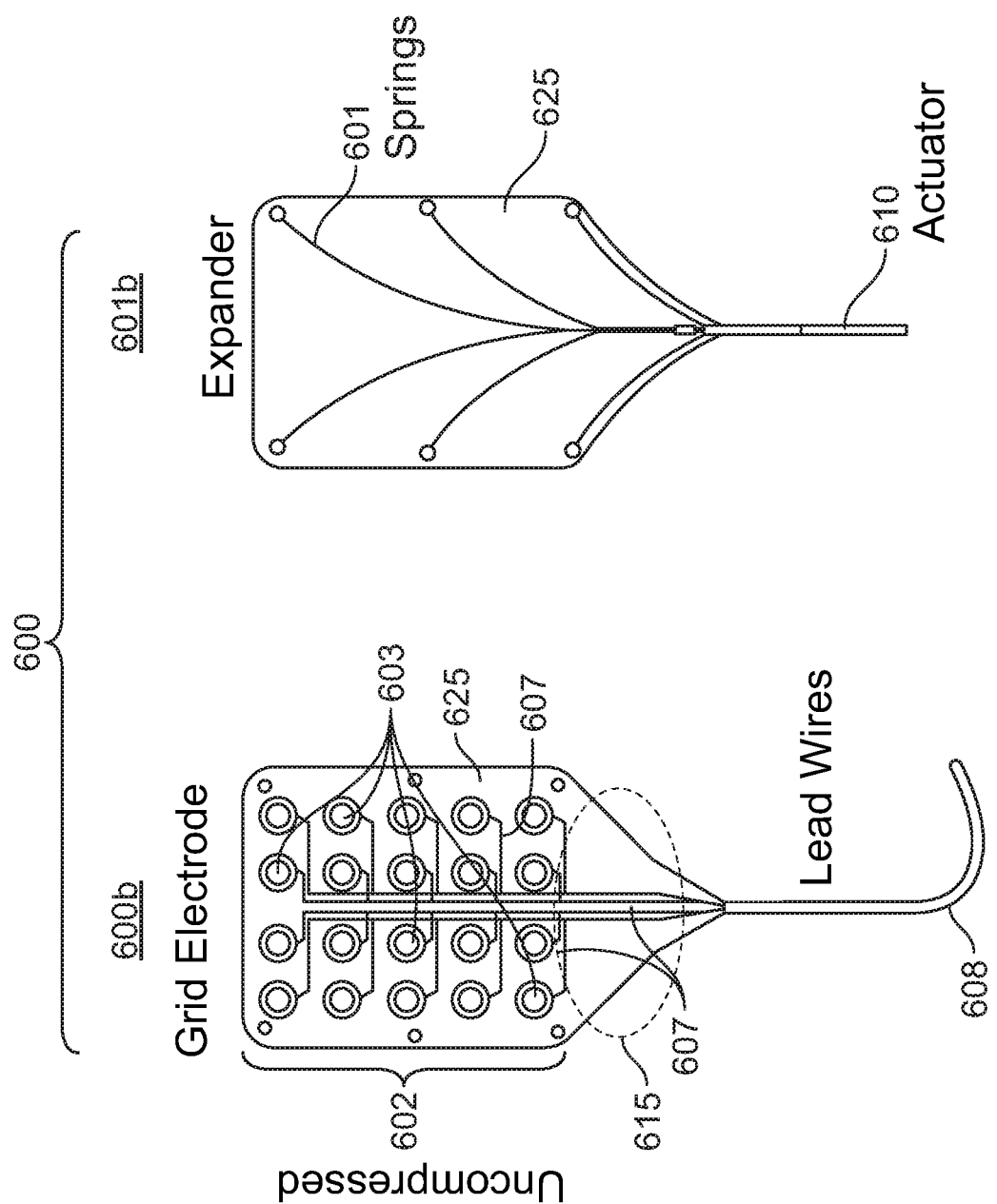
FIG. 6C is an illustration of the electrode system of FIGS. 6A and 6B, in uncompressed or expanded form, in accordance with some embodiments of the present specification.

In an embodiment, the electrode array 602 is a multi-contact grid electrode consisting of an array of contacts 603, each of which has a lead wire 607 (visible in FIG. 6C). The lead wires 607 are bundled into one or more pigtails 608 and terminated in a multi-contact connector. Within or alongside the compressed electrode array 602 is a guide wire 606. In an alternate configuration, a plunger would follow the lead wires 607 to the proximal end 602b of the compressed electrode array 602. Operationally, after the cannula 604 has been inserted into a patient's skull, it is pulled back, releasing or unfurling the compressed electrode array 602 using the guide wire 606 or the plunger to keep the electrode array 602 at the desired location and depth. The electrode system 600 also includes, in some embodiments, an actuator 610.

Figure 6D:
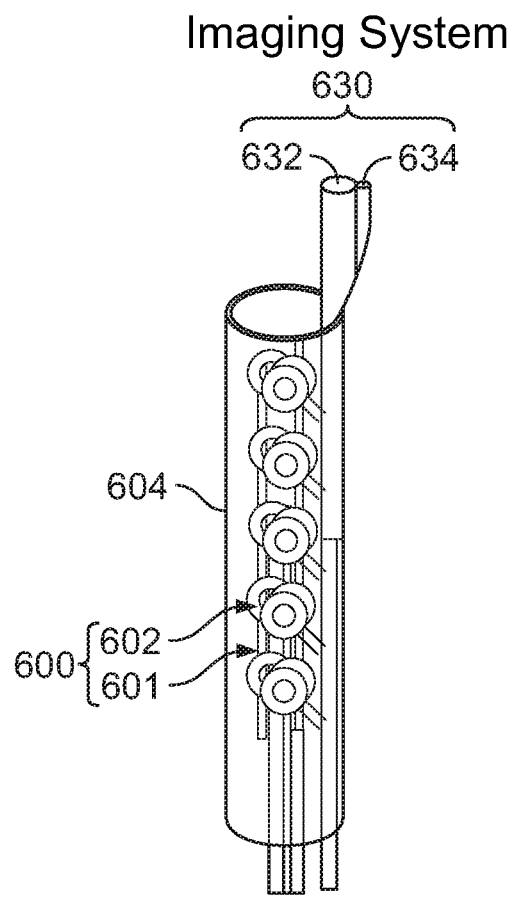
FIG. 6D illustrates the visualization or imaging system protruding beyond a distal end of the cannula, in accordance with some embodiments of the present specification.
Figure 6E:
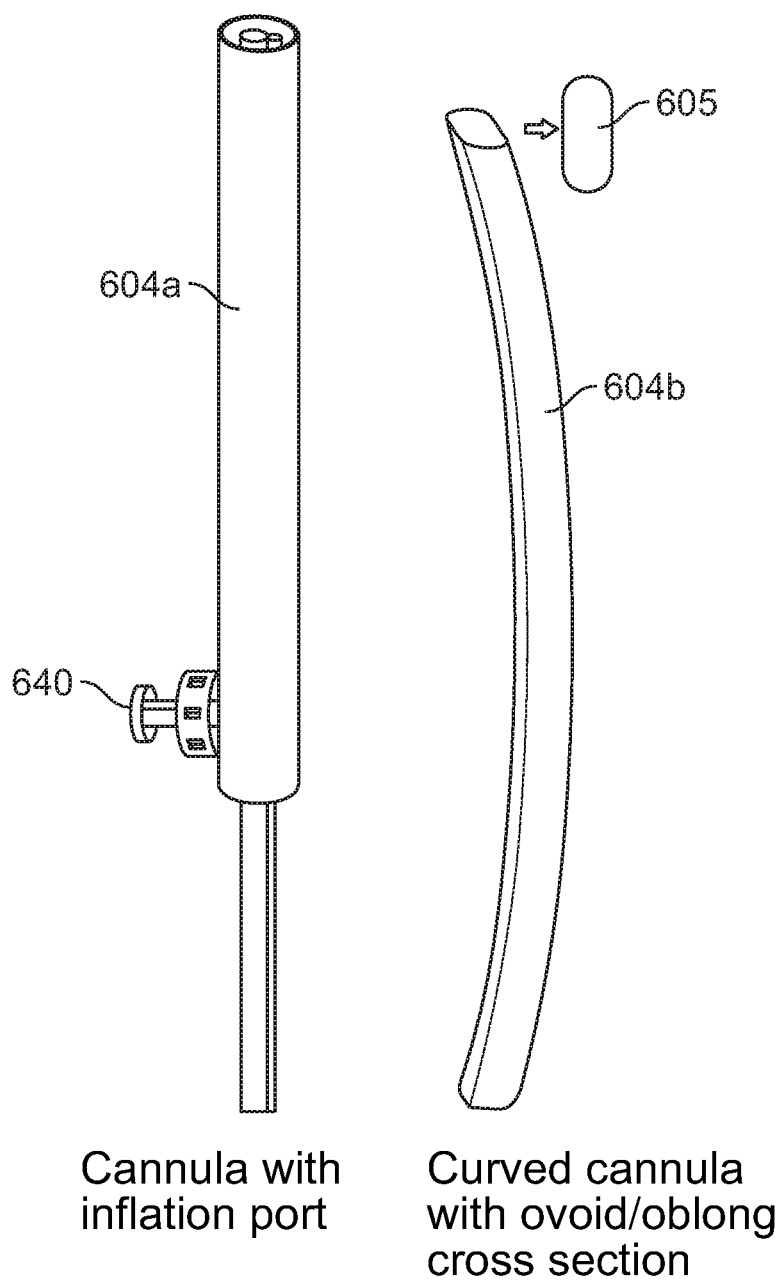
FIG. 6E illustrates a first cannula with a port and a second cannula with an oblong/ovoid cross-section and a curved length, in accordance with some embodiments of the present specification.

In some embodiments, as shown in FIG. 6A, the cannula 604 may have a circular cross-section and a straight elongate body. However, in alternate embodiments, as shown in FIG. 6E, the cannula 604b may have an ovoid or oblong cross-section 605 and may be curved along its length to transit a surface of the brain around a curvature of the brain. In some embodiments, as shown in FIG. 6E, a port 640 in the cannula 604a may provide compressed gas to generate a brain-cranium gap for inserting the cannula 604a and visualizing the insertion and deployment trajectory.

In some embodiments, the visualization or imaging system 630 comprises a front-pointing viewing element 632 to visualize and image, based on its field of view, insertion and deployment of the electrode array 602 into the patient's skull and at least one illuminator 634 for illuminating a field of view of the front-pointing viewing element 632. In some embodiments, the front-pointing viewing element 632 is a digital camera comprising a front-pointing image sensor such as, but not limited to, a Charge Coupled Device (CCD) or a Complementary Metal Oxide Semiconductor (CMOS) image sensor.

In embodiments, the front-pointing viewing element 632 is positioned at a distal tip of an elongated sheath 633. During deployment, the elongated sheath 633 is inserted through a proximal end of the cannula 604 such that the front-pointing viewing element 632 lies within, proximal or protrudes a distal end of the cannula 604.

In an embodiment, the front-pointing viewing element 632 is mounted on a circuit board, which supplies it with necessary electrical power, and in an embodiment, generates still images and/or video feeds captured by the image sensor. In one embodiment, the circuit board is connected to a set of electrical cables (not shown) which are threaded through a channel running through the elongated sheath 633. The set of electrical cables emanate from a proximal end of the sheath 633 for connection to a computing device and associated display, monitor or screen. In various embodiments, the computing device is configured with hardware and/or software to receive and process image and/or a video feed acquired by the front-pointing viewing element 632 and display the image and/or video feed on an associated display, monitor or screen. In an embodiment, the front-pointing viewing element 632 has a lens assembly mounted on top of it and provides the necessary optics for receiving images. In one configuration, the lens assembly includes a plurality of lenses, static or movable, which provide a field of view ranging from 90 degrees to 180 degrees.

In some embodiments, the at least one illuminator 634 may include a light-emitting diode (LED), which may be a white light LED, an infrared light LED, a near infrared light LED, an ultraviolet light LED or any other LED. In such embodiments, the at least one LED may be coupled to the same circuit board on which the front-pointing viewing element 632 is mounted and positioned proximate the front-pointing viewing element 632. In some embodiments, the at least one illuminator 634 may be a fiber optic illuminator that transmits light generated from remote sources. In such embodiments, the fiber optic illuminator is inserted through the cannula 604 and positioned next to the front-pointing viewing element 632.

During deployment, the at least one illuminator 634 (that is, the LED or the fiber optic illuminator) together with the front-pointing viewing element 632 are inserted through the proximal end of the cannula 604 so as to lie proximate or protrude the distal end of the cannula 604. In various embodiments, the visualization or imaging system 630 (that is, the front-pointing viewing element 632 and the at least one illuminator 634) rests in the cannula 604 during insertion, but may be protruded beyond the distal end of the cannula 604 after the cannula 604 is positioned for deployment—as can be seen in FIG. 6D. In some embodiments, the contents (that is, the visualization or imaging system 630 and the electrode system 600) of the cannula 604 are stacked such that the visualization or imaging system 630 can be deployed first. The imaging system 620 once deployed can be moved laterally to provide clearance for the electrode system 600. This allows more room (or clearance) for the electrode system 600 without increasing the cross-sectional size of the cannula 604 while also allowing visualization of the deployment. Once the electrode system 600 is fully deployed the front-pointing viewing element 632 fits again through the cannula 604 along with electrode leads or lead wires when the cannula 604 is removed.

FIG. 6B is an illustration of the electrode system 600 of FIG. 6A, with the electrode array 602 in compressed form and removed from the cannula 604, in accordance with some embodiments of the present specification. The electrode array 602 is shown in a compressed configuration with the array of contacts 603 and the lead wires (or electrode leads) 607 bundled into at least one pigtail 608. The electrode leads are flexible and resist breakage when the electrode array 602 is compressed and uncompressed.

In embodiments, the electrode array 602 is attached or coupled to a substrate 625 having dimensions of 2 cm to 15 in an uncompressed form. The substrate 625 of the electrode array 602 is of sufficient strength and flexibility so that the array 602 will not fragment during insertion or removal. In some embodiments, if necessary, reinforcing filaments can be added to the substrate which will effectively distribute the forces that come into play during compression and release of the electrode array 602. In embodiments, the substrate 625 is biocompatible for temporary implantation and can be sterilized.

In various embodiments, the substrate 625 is made of flexible biocompatible material such as silicone rubber and with conductive contacts as are currently used for grid electrodes such as stainless steel, platinum or carbon. The geometry can be variable both in size and shape as is currently supported by invasively placed cortical grid electrodes. The contacts may also be placed asymmetrically to accommodate optimal spring positions and to allow ease of placement and removal. The plurality of electrodes or contacts 603 are distributed across the substrate 625. Each electrode or contact, of the plurality of electrodes or contacts 603, has dimensions of 0.1 mm to 10 mm. In some embodiments, the electrodes or contacts 603 are preferably distributed such that there is at least 1 electrode or contact 603 for every 0.1 mm$^2$ to 20 mm$^2$ of the substrate 625. In various embodiments, the electrodes or contacts 603 are attached or coupled to the substrate 625 using any attachment mechanism known in the art.

In various embodiments, the electrode array 602 is compressed into a plurality of configurations such as, but not limited to, a first configuration wherein the array 602 is rolled up, a second configuration wherein the array 602 is folded in an accordion-like manner, a third configuration wherein the array 602 is compressed in a serpentine manner, a fourth configuration wherein the array 202 is squeezed in a tube-like manner or in other ways or configurations that combine or are different from these three exemplary configurations.

Also shown in FIG. 6B is the inserter 601 in compressed form along with the actuator 610. In various embodiments, the inserter 601 is removably attached or coupled to the electrode array 602 and/or the substrate 625. In some embodiments, in a compressed state, the substrate 625, in combination with the electrodes/contacts 603, the inserter 601 and the lead wires 607, have dimensions that are less than the substrate 625 and electrodes/contacts 603 in uncompressed form.

FIG. 6C is an illustration of the electrode system 600 of FIGS. 6A and 6B, in uncompressed or expanded form, in accordance with some embodiments of the present specification. As described earlier, the grid electrode array 602 consists of an array of contacts 603, each of which has a lead wire 607. The lead wires 607 are bundled into one or more pigtails 608 and terminated in a multi-contact connector. The pigtails 608 pass through the patient's skull and skin, via a burr hole, and the multi-contact connector is external to the patient. In some embodiments, the grid electrode array 602 is fabricated on the substrate 625 which is thin and flexible so as to conform to the surface of the patient's brain when applied, and which can be compressed, rolled or folded into a tube-like structure for insertion.

An uncompressed or unfurled configuration 601b of the inserter 601 is also shown wherein the inserter 601 is embedded/built into, coupled or attached to the flexible substrate 625 that supports the grid electrode array 602. Unfurling or unfolding of the electrode array 602 requires it to roll across or slide across the surface of the patient's brain. In accordance with an aspect of the present specification, the inserter 601 is embodied as a spring which is gradually released as the cannula 604 (FIG. 6A) is retracted thereby unfurling the electrode array 602.

The inserter 601 embodied as one or more springs, shown in uncompressed form in FIG. 6C, also employs a mechanical actuator 610 to aid unfurling of the compressed electrode system 600 (FIG. 6B) into an uncompressed state 600b (FIG. 6C) for placement on the surface of a patient's brain, in accordance with some embodiments of the present specification. The actuator 610 is held in place when the cannula 604 (FIG. 6A) is retracted and subsequently released from the spring for removal of the actuator 610.

In some embodiments, referring back to FIG. 6C, a proximal portion 615 of the substrate 625 has a tapered shape to facilitate ease of movement through the burr hole during retraction of the cannula 604 (FIG. 6A). Additionally, in some embodiments, the electrode contacts 603 as well as the inserter 610, embodied as one or more springs, are also distributed on the substrate 625 in a tapered configuration to facilitate ease of movement of the electrode system 600 through the burr hole during retraction of the cannula 604 (FIG. 6A).

The spring actuated embodiment expands towards its pre-compressed position taking the electrode substrate along. As shown in FIG. 6C, the actuator 610 is coupled to a collapsible or expandable spring (or inserter 601).

In some embodiments, the spring is left in place within the substrate 625 along with the electrode array 602 upon deployment in the patient's brain and provides a collapsing mechanism when the electrode array 602 is removed (such as by teasing and tugging at the at least one pigtail 608). In alternate embodiments, the spring can be pulled out or released from the substrate 625 once the electrode array 602 is deployed and its desired placement is confirmed.

Referring again to FIG. 6C, in some embodiments, a distribution of the plurality of electrodes or contacts 603 on the substrate 625 may be asymmetrical as locations of the contacts 603 may be required to be shifted to avoid overlap with spring locations.

Figure 7:
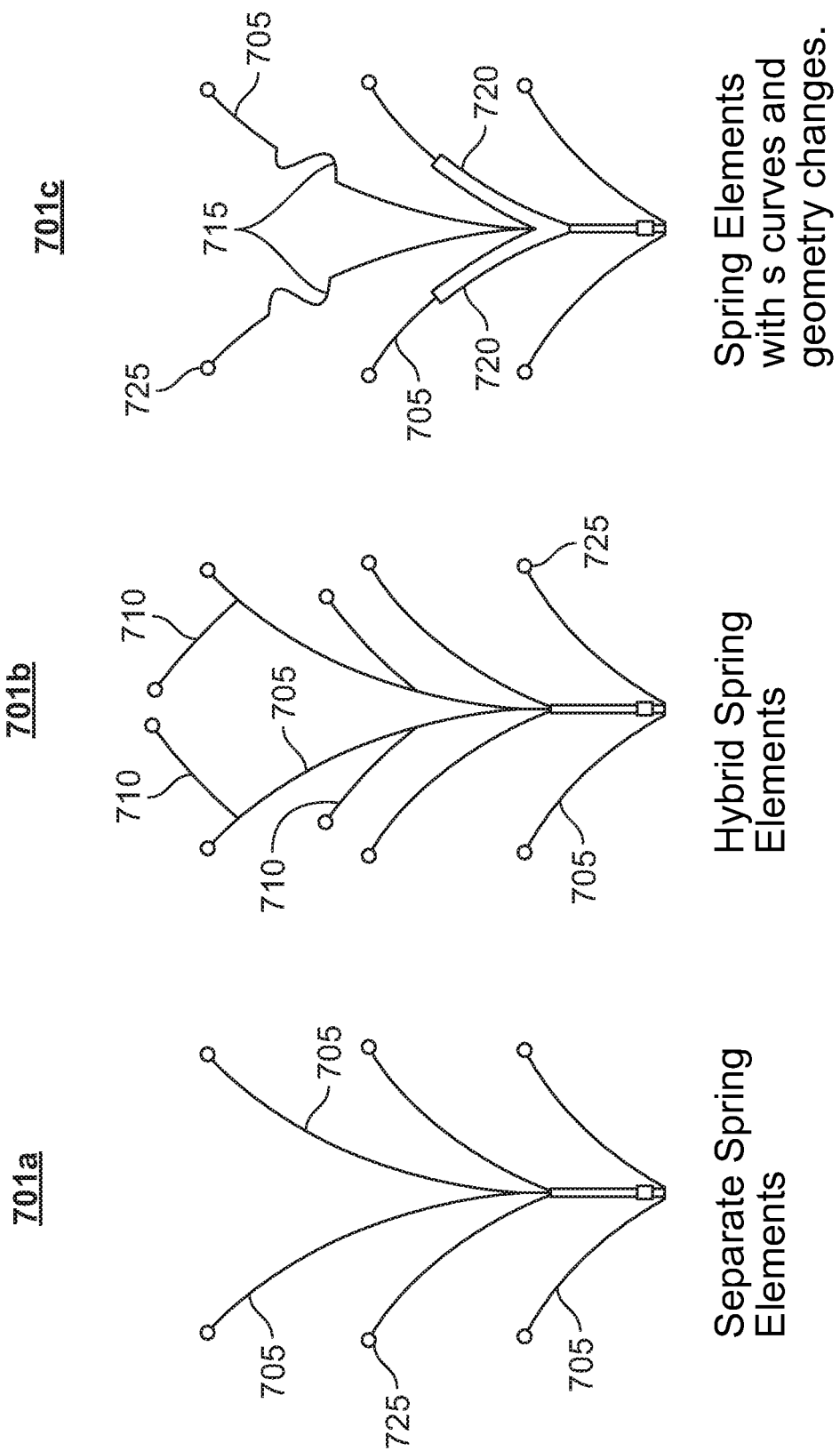
FIG. 7 shows first, second and third configurations of a spring functioning as an inserter, in accordance with some embodiments of the present specification; and, FIG. 8 is a workflow describing exemplary steps for inserting, expanding, verifying, and extracting the electrode system of FIG. 6A, in accordance with some embodiments of the present specification.

In various embodiments, the spring (inserter 601) may be configured in a plurality of forms. FIG. 7 shows first, second and third configurations 701a, 701b, and 701c of a spring functioning as an inserter, in accordance with some embodiments of the present specification. In the first configuration 701a, the spring comprises a plurality of separate spring elements 705. In the second configuration 701b, the spring comprises a plurality of hybrid elements such that at least one sequential or child spring element 710 may be attached or branch off along a length of at least one preceding or parent spring element 705.

In the third configuration 701c, the spring is shown incorporating first and second features that enable modulation or adjustment of the spring constant of the spring. In embodiments, the spring constant of each spring element 705 may be adjusted for its position along the grid electrode array. In some embodiments, this is accomplished by adding a first feature in the form of S-curves 715 to one or more spring elements 705. In some embodiments, this is accomplished by incorporating a second feature that deals with modifying or changing a geometry 720 (comprising, cross-sectional shape and/or size/radius) along a length of one or more spring elements 705. It should be appreciated, that attaching at least one child spring element 710 to at least one parent spring element 705, as shown in the second configuration 701b, also enables modulation of the spring constant.

In some embodiments, contacts are placed asymmetrically to accommodate optimal spring positions and to allow ease of placement and removal.

While the illustrations of the first, second and third configurations 701*a*, 701*b*, 701*c* are of relatively simple spring geometries, it should be noted that in various alternate embodiments the spring geometries may be more complex to optimize both the unfolding process and to reduce forces and risk of injury. It should be appreciated, however, that in a preferred embodiment, there is at least one first spring element having a distal end in physical communication with a first corner or edge of the electrode array (such as the left side) and at least one second spring element having a distal end in physical communication with a second corner or edge of the electrode array (such as the right side) where 1) the first corner or edge is positioned opposite the second corner or edge, 2) the distal end of the at least one first spring element is configured to move separate and distinct from the distal end of the at least one second spring element, preferably in an opposing direction, and 3) a proximal end of the at least one first spring element and the at least one second spring element are connected to a common member. It should further be appreciated that additional spring elements may be attached to areas of the electrode array proximate the first corner or edge and proximate the second corner or edge where each of those additional spring elements are attached, at a proximal end, to the same common member.

In embodiments, the spring elements 705, 710 and features 715, 720 may be fabricated from materials such as, for example, plastic, metal or carbon fiber. In embodiments, tips 725 of the spring elements 705, 710 are embedded/built into, attached or coupled to the electrode substrate (substrate 625 of FIG. 6C), and the tips 725 themselves are shaped, such as for example with a ball end or a substantially spherical or bulbous end, to reduce risk of injury to the brain tissue. In some embodiments, the spring is left in place within the substrate along with the electrode array upon deployment in the patient's brain and provides a collapsing mechanism when the electrode array is removed. In alternate embodiments, the spring can be pulled out or released from the substrate once the electrode array is deployed and its desired placement is confirmed.

Figure 8:
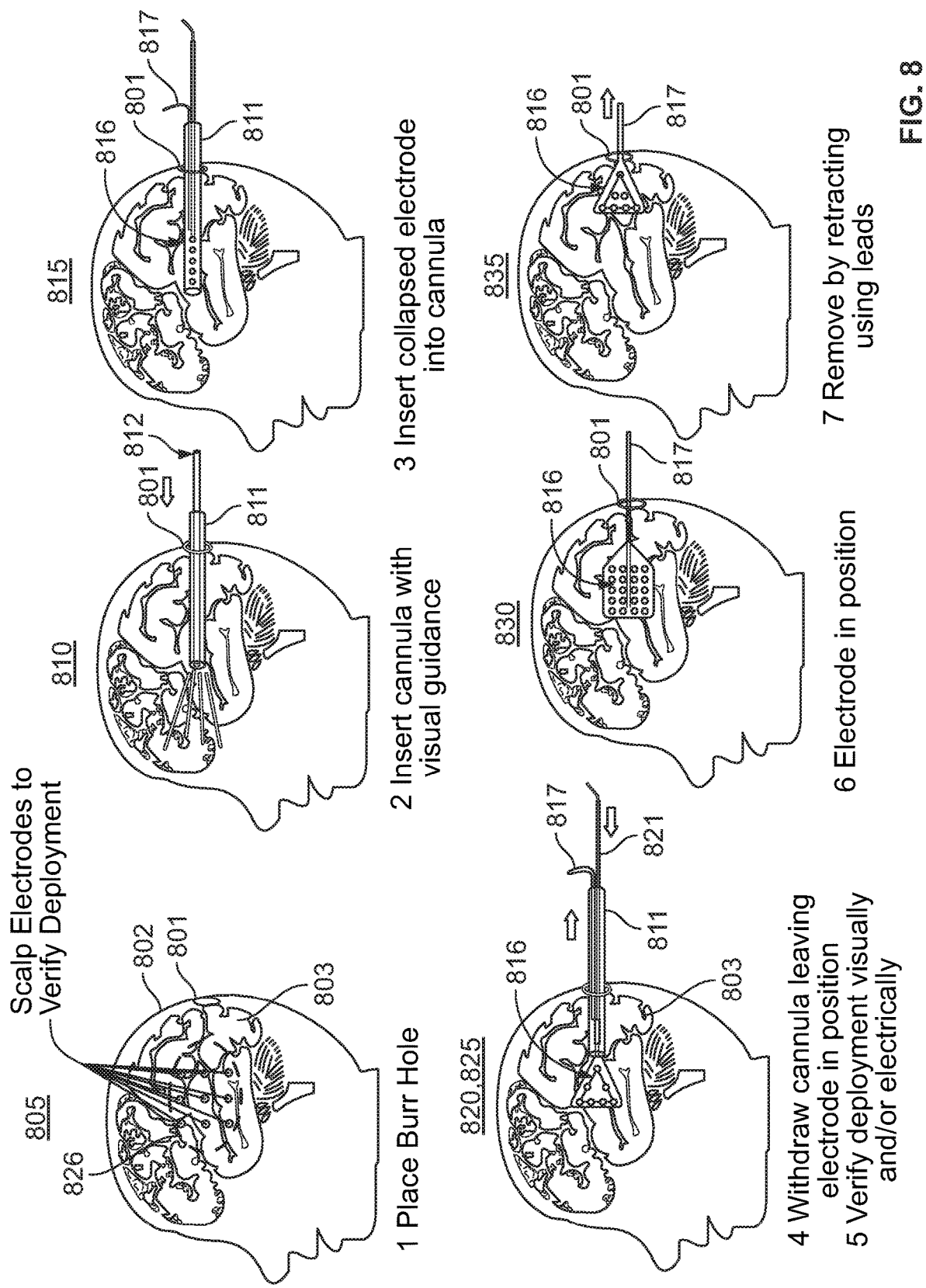

FIG. 8 is a workflow describing exemplary steps for inserting, expanding, verifying, and extracting the electrode system, in accordance with some embodiments of the present specification. At step 805, an insertion, access or burr hole 801 is formed or created in a patient's skull or cranium 802 at a desired location and of a desired depth so as to enable access to a surface of the patient's brain or cortex 803.

At step 810, a cannula 811 is inserted through the hole 801 with the help or guidance of a visualization or imaging system 812 comprising a front-pointing viewing element (such as a digital camera) and at least one illuminator (such as an LED of a fiber optic illuminator). In some embodiments the cannula 811 may have a circular cross-section and a straight elongate body. However, in alternate embodiments, the cannula 811 may have an ovoid or oblong cross-section and may be curved along its length.

At step 815, in some embodiments, an assembly 816 of an inserter attached to an electrode array is compressed or collapsed and slid or inserted into the access or burr hole 801 through the cannula 811. In alternate embodiments, a compressed assembly 816 of the inserter attached to the electrode array along with the visualization or imaging system 812 is prepackaged or stacked within the cannula 811 and ready for deployment. In some embodiments, the inserter is embodied in the form of a collapsible or expandable spring. A plurality of lead wires or electrode leads emanating from a plurality of electrode contacts of the electrode array, are bundled together into at least one pigtail 817. In some embodiments, the cannula 811 includes an orientation mark or indicator (at distal and/or proximal ends of the cannula 811) so that a proper contact surface or side of the electrode array is deployed with contacts against the brain or cortex 803 when uncompressed. This is advantageous since the surfaces of the electrode array are not reversible. In alternate embodiments, where the cannula 811 is curved along its length, the orientation mark or indicator is not required as the bearing of the contact surface or side of the electrode array is implied to be a concave side of the cannula 811. Accordingly, the assembly 816 within the cannula 811 is prepackaged such that the contact surface or side of the electrode array resides towards the concave side of the curved cannula 811.

At step 820, the cannula 811 is slid back and partially withdrawn leaving and exposing the assembly 816 of the electrode array and the inserter in place. As the cannula 811 is withdrawn, the compressed assembly 816 expands, unfurls or unfolds due to a recoiling or releasing action of the spring (inserter) thereby unfurling the electrode array over a surface of the patient's brain or cortex 803. In some embodiments, a guide wire 821 is utilized to keep the assembly 816 at the desired location and depth while the cannula 811 is being retracted, slid back or withdrawn. It should be appreciated that pushing on or holding the guide wire 821 in place, while the cannula 811 is being retracted, keeps the electrode array and the inserter in place and enables the spring inserter to un-compress or unfurl and spread the electrode array.

At step 825, the location or position of the deployed or unfurled electrode array is verified to ensure that the location or position is indeed the intended, targeted or desired position. In embodiments, verification of the deployment is performed visually (using the visualization or imaging system 812) and/or electrically. For electrical verification, a plurality of surface electrodes 826 (shown in the figure associated with step 805) are placed on the patient's scalp such that the surface electrodes 826 are over the expected, intended, desired or target location where the electrode array is supposed to have been implanted and deployed over the surface of the patient's brain or cortex 803. Lead wires from the electrode array, bundled into at least one pigtail 817, and are in electrical communication with an EEG amplifier. The surface electrodes 826 are in electrical communication with an electrical pulse generator that causes pulsed electric field to be generated across the plurality of surface electrodes 826. The pulsed electric field generated across the plurality of surface electrodes 826 is detected as a signal by each implanted grid electrode (of the electrode array). The location of each grid electrode is calculated from such signal using an inverse localization and statistical comparison to an expected, intended, desired or target location.

At step 830, the cannula 811 is completely withdrawn or retracted leaving the assembly 816 at the target location. As shown, the pigtail 817 extends from the hole 801. Finally when desired, at step 835, the assembly 816 is removed or extracted through the hole 801 by teasing it out using the at least one pigtail 817 of the electrode array. In embodiments, the flexible substrate of the electrode array and the inserter, embodied in the form of the spring, will collapse in on itself and exit via the insertion path and insertion or burr hole 801.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

I claim:

1. A system for deploying an electrode array at a target location within a patient's cranium through a hole formed in the patient's cranium, the system comprising:
a substrate;
an array of electrodes attached to the substrate;
an inserter attached to the substrate, wherein the inserter, the substrate, and the array of electrodes are configured in a first compressed state and wherein the inserter is configured to expand from the first compressed state to a second uncompressed state;
a first actuator coupled to the inserter, wherein the first actuator is configured to be accessible outside the patient's cranium and further configured such that, when a force is applied to the first actuator, in a first direction, the inserter expands, thereby causing the inserter, the substrate, and the array of electrodes to be in the second uncompressed state; and
a cannula configured to accommodate the inserter, the substrate and the array of electrodes in the first compressed state and configured to release the inserter, the substrate and the array of electrodes through the hole and within the patient's cranium at the target location.

2. The system of claim 1, wherein, in the first compressed state, the substrate and array of electrodes have a width that is less than a width of the substrate and array of electrodes in the second uncompressed state.

3. The system of claim 1, wherein the array of electrodes comprises a plurality of contacts having associated lead wires, and wherein each of said lead wires is connected to a terminal on an electrical device.

4. The system of claim 1, wherein the first actuator is configured such that, when a force is applied to the first actuator in a second direction, the inserter compresses, thereby causing the inserter, the substrate, and the array of electrodes to be in the first compressed state.

5. The system of claim 1, wherein the inserter comprises at least a first spring element and a second spring element, wherein a distal end of the first spring element is attached to a first edge of the substrate, wherein a distal end of the second spring element is attached to a second edge of the substrate, and wherein the first edge opposes the second edge.

6. The system of claim 5, wherein a proximal end of the first spring element and a proximal end of the second spring element are connected to a common member.

7. The system of claim 1, wherein the inserter comprises a multi-segmented cantilever coupled to the first actuator and a second actuator.

8. The system of claim 7, wherein the multi-segmented cantilever is configured to expand when the first actuator is pulled in a first direction and the second actuator is pushed in an opposing second direction.

9. The system of claim 1, wherein the substrate has a tapered proximal portion configured to facilitate ease of extraction of the substrate through the hole.

10. The system of claim 1, wherein the cannula includes a mark to facilitate a proper orientation of a contact surface of the array of electrodes during release of the inserter, the substrate and the array of electrodes.

11. The system of claim 1, wherein the cannula has an ovoid cross-section and is curved along its length.

12. The system of claim 1, wherein the cannula includes a port configured to provide compressed gas to generate a brain-cranium gap for inserting the cannula through the hole.

13. The system of claim 1, wherein the cannula further accommodates a front-pointing viewing element and at least one illuminator.

14. A method of deploying an electrode array at a target location within a patient's cranium through a hole formed in the patient's cranium, the method comprising:
obtaining an electrode array system, wherein the electrode array system comprises a cannula having a lumen, a substrate, an array of electrodes attached to the substrate, and an inserter attached to the substrate, wherein the substrate, the array of electrodes, and the inserter are positioned in the lumen in a first compressed state;
inserting the cannula through the hole;
sliding the cannula backwards while positioning the inserter, the substrate, and the array of electrodes at the target location; and
causing the inserter, the substrate and the array of electrodes to transition from the first compressed state to a second uncompressed state at the target location by moving a first actuator attached to the inserter, wherein the first actuator is configured to be accessible outside the patient's cranium and further configured such that, when a force is applied to the first actuator, in a first direction, the inserter expands, thereby causing the inserter, the substrate, and the array of electrodes to be in the second uncompressed state.

15. The method of claim 14, wherein, in the first compressed state, the substrate and array of electrodes have a width that is less than a width of the substrate and the array of electrodes in the second uncompressed state.

16. The method of claim 14, wherein the array of electrodes comprises a plurality of contacts having associated lead wires and wherein each of said lead wires is connected to a terminal on an electrical device.

17. The method of claim 14, wherein the first actuator is further configured such that, when a force is applied to the first actuator, in a second direction, the inserter compresses, thereby causing the inserter, the substrate, and the array of electrodes to be in the first compressed state.

18. The method of claim 14, wherein the inserter comprises at least a first spring element and a second spring element, wherein a distal end of the first spring element is attached to a first edge of the substrate, wherein a distal end of the second spring element is attached to a second edge of the substrate, and wherein the first edge opposes the second edge.

19. The method of claim 18, wherein a proximal end of the first spring element and a proximal end of the second spring element are connected to a common member.

20. The method of claim 14, wherein the inserter comprises a multi-segmented cantilever coupled to an actuator.

21. The method of claim 20, wherein the multi-segmented cantilever is configured to expand when the first actuator is pulled in a first direction and configured to contract when the first actuator is pulled in a second direction.

22. The method of claim 14, further comprising causing the inserter, the substrate and the array of electrodes to transition from the second uncompressed state to the first compressed state at the target location.

23. The method of claim 22, wherein the inserter, the substrate and the array of electrodes transitions from the second uncompressed state to the first compressed state by moving the first actuator in physical communication with the inserter.

24. The method of claim 22, further comprising removing the cannula and the inserter through the hole.

25. The method of claim 22, further comprising extracting the array of electrodes through the hole.

26. The method of claim 14, further comprising verifying a physical position of at least one of the inserter, the substrate or the array of electrodes within the patient's cranium.

27. A method of deploying an electrode array at a target location onto a patient's cortex through a burr hole formed on the patient's cranium, the method comprising:
    directing gas into the patient's cranium to generate a brain-cranium gap for inserting the cannula through the burr hole;
    inserting a cannula through said burr hole, wherein the cannula accommodates an inserter and an array of electrodes, and wherein said inserter and array of electrodes are in a first compressed state;
    sliding the cannula backwards while positioning said inserter and array of electrodes in said first compressed state at said target location;
    causing said array of electrodes to be in a second uncompressed state at said target location; and
    verifying said positioning of said inserter and array of electrodes at said target location.

28. The method of claim 27, further comprising removing the cannula and the inserter through the burr hole.

29. The method of claim 28, further comprising extracting the array of electrodes through the burr hole.

30. A system for deploying an electrode array at a target location within a patient's cranium through a hole formed in the patient's cranium, the system comprising:
    a substrate;
    an array of electrodes attached to the substrate;
    an inserter attached to the substrate, wherein the inserter, the substrate, and the array of electrodes are configured in a first compressed state and wherein the substrate and the array of electrodes are configured to expand from the first compressed state to a second uncompressed state;
    a cannula configured to accommodate the inserter, the substrate and the array of electrodes in the first compressed state and configured to release the inserter, the substrate and the array of electrodes through the hole and within the patient's cranium at the target location, wherein the cannula further comprises a port configured to direct gas into the patient's cranium to generate a brain-cranium gap for inserting the cannula through the hole.

31. The system of claim 30, further comprising a first actuator coupled to the inserter, wherein the first actuator is configured to be accessible outside the patient's cranium and is further configured such that, when a force is applied to the first actuator, in a first direction, the inserter expands, thereby causing the substrate and the array of electrodes to be in the second uncompressed state.

32. The system of claim 31, wherein the first actuator is configured such that, when a force is applied to the first actuator in a second direction, the inserter compresses, thereby causing the substrate and the array of electrodes to be in the first compressed state.

33. The system of claim 30, wherein, in the first compressed state, the substrate and array of electrodes have a width that is less than a width of the substrate and array of electrodes in the second uncompressed state.

34. The system of claim 30, wherein the array of electrodes comprises a plurality of contacts having associated lead wires, and wherein each of said lead wires is connected to a terminal on an electrical device.

35. The system of claim 30, wherein the inserter comprises at least a first spring element and a second spring element, wherein a distal end of the first spring element is attached to a first edge of the substrate, wherein a distal end of the second spring element is attached to a second edge of the substrate, and wherein the first edge opposes the second edge.

36. The system of claim 35, wherein a proximal end of the first spring element and a proximal end of the second spring element are connected to a common member.

37. The system of claim 30, wherein the inserter comprises a multi-segmented cantilever coupled to the first actuator and a second actuator.

38. The system of claim 37, wherein the multi-segmented cantilever is configured to expand when the first actuator is pulled in a first direction and the second actuator is pushed in an opposing second direction.

39. The system of claim 30, wherein the substrate has a tapered proximal portion configured to facilitate ease of extraction of the substrate through the hole.

40. The system of claim 30, wherein the cannula comprises a mark to facilitate a proper orientation of a contact surface of the array of electrodes during release of the inserter, the substrate and the array of electrodes.

41. The system of claim 30, wherein the cannula has an ovoid cross-section and is curved along its length.

42. The system of claim 30, wherein the cannula further accommodates a front-pointing viewing element and at least one illuminator.

* * * * *